United States Patent
Sgroi, Jr. et al.

(10) Patent No.: US 11,426,168 B2
(45) Date of Patent: Aug. 30, 2022

(54) TROCAR COUPLING ASSEMBLIES FOR A SURGICAL STAPLER

(71) Applicant: Covidien LP, Mansfield, MA (US)

(72) Inventors: Anthony Sgroi, Jr., Wallingford, CT (US); Joseph Eisinger, Northford, CT (US); Ramiro Cabrera, Cheshire, CT (US); David Valentine, Hamden, CT (US); Patrick Mozdzierz, Glastonbury, CT (US)

(73) Assignee: Covidien LP, Mansfield, MA (US)

( * ) Notice: Subject to any disclaimer, the term of this patent is extended or adjusted under 35 U.S.C. 154(b) by 529 days.

(21) Appl. No.: 16/503,726

(22) Filed: Jul. 5, 2019

(65) Prior Publication Data
US 2021/0000472 A1    Jan. 7, 2021

(51) Int. Cl.
A61B 17/064 (2006.01)
A61B 17/115 (2006.01)
A61B 17/072 (2006.01)
A61B 17/11 (2006.01)

(52) U.S. Cl.
CPC ........ *A61B 17/1155* (2013.01); *A61B 17/072* (2013.01); *A61B 17/1114* (2013.01); *A61B 2017/07257* (2013.01); *A61B 2017/07271* (2013.01); *A61B 2017/07285* (2013.01)

(58) Field of Classification Search
CPC .................. A61B 17/1155; A61B 2017/00477
See application file for complete search history.

(56) References Cited

U.S. PATENT DOCUMENTS

| 2,777,340 A | 1/1957 | Hettwer et al. |
| 2,957,353 A | 10/1960 | Babacz |
| 3,111,328 A | 11/1963 | Di Rito et al. |
| 3,695,058 A | 10/1972 | Keith, Jr. |
| 3,734,515 A | 5/1973 | Dudek |
| 3,759,336 A | 9/1973 | Marcovitz et al. |
| 4,162,399 A | 7/1979 | Hudson |
| 4,606,343 A | 8/1986 | Conta et al. |
| 4,705,038 A | 11/1987 | Sjostrom et al. |
| 4,722,685 A | 2/1988 | de Estrada et al. |
| 4,823,807 A | 4/1989 | Russell et al. |
| 4,874,181 A | 10/1989 | Hsu |
| 5,129,118 A | 7/1992 | Walmesley |
| 5,129,570 A | 7/1992 | Schulze et al. |

(Continued)

FOREIGN PATENT DOCUMENTS

| CA | 2451558 A1 | 1/2003 |
| CN | 1547454 A | 11/2004 |

(Continued)

OTHER PUBLICATIONS

The extended European Search Report dated Feb. 8, 2021 issued in corresponding EP Appln. No 20183412.4.

*Primary Examiner* — Eyamindae C Jallow

(74) *Attorney, Agent, or Firm* — Carter, DeLuca & Farrell LLP

(57) ABSTRACT

A trocar coupling assembly includes a housing disposable in a tubular shaft of a surgical stapler. The housing has opposed openings defining a passage through the housing that is capable of receiving a trocar assembly therein. A release button is accessible through the tubular shaft for transitioning the trocar coupling assembly between a locked configuration and an unlocked configuration.

15 Claims, 16 Drawing Sheets

(56) References Cited

U.S. PATENT DOCUMENTS

| | | |
|---|---|---|
| 5,152,744 A | 10/1992 | Krause et al. |
| 5,301,061 A | 4/1994 | Nakada et al. |
| 5,312,023 A | 5/1994 | Green et al. |
| 5,326,013 A | 7/1994 | Green et al. |
| 5,350,355 A | 9/1994 | Sklar |
| 5,383,874 A | 1/1995 | Jackson et al. |
| 5,383,880 A | 1/1995 | Hooven |
| 5,389,098 A | 2/1995 | Tsuruta et al. |
| 5,395,033 A | 3/1995 | Byrne et al. |
| 5,400,267 A | 3/1995 | Denen et al. |
| 5,411,508 A | 5/1995 | Bessler et al. |
| 5,413,267 A | 5/1995 | Solyntjes et al. |
| 5,427,087 A | 6/1995 | Ito et al. |
| 5,433,721 A | 7/1995 | Hooven et al. |
| 5,467,911 A | 11/1995 | Tsuruta et al. |
| 5,476,379 A | 12/1995 | Disel |
| 5,487,499 A | 1/1996 | Sorrentino et al. |
| 5,518,163 A | 5/1996 | Hooven |
| 5,518,164 A | 5/1996 | Hooven |
| 5,526,822 A | 6/1996 | Burbank et al. |
| 5,529,235 A | 6/1996 | Boiarski et al. |
| 5,535,934 A | 7/1996 | Boiarski et al. |
| 5,535,937 A | 7/1996 | Boiarski et al. |
| 5,540,375 A | 7/1996 | Bolanos et al. |
| 5,540,706 A | 7/1996 | Aust et al. |
| 5,542,594 A | 8/1996 | McKean et al. |
| 5,549,637 A | 8/1996 | Crainich |
| 5,553,675 A | 9/1996 | Pitzen et al. |
| 5,562,239 A | 10/1996 | Boiarski et al. |
| 5,564,615 A | 10/1996 | Bishop et al. |
| 5,609,560 A | 3/1997 | Ichikawa et al. |
| 5,626,587 A | 5/1997 | Bishop et al. |
| 5,632,432 A | 5/1997 | Schulze et al. |
| 5,645,209 A | 7/1997 | Green et al. |
| 5,647,526 A | 7/1997 | Green et al. |
| 5,653,374 A | 8/1997 | Young et al. |
| 5,658,300 A | 8/1997 | Bito et al. |
| 5,662,662 A | 9/1997 | Bishop et al. |
| 5,667,517 A | 9/1997 | Hooven |
| 5,693,042 A | 12/1997 | Boiarski et al. |
| 5,704,534 A | 1/1998 | Huitema et al. |
| 5,713,505 A | 2/1998 | Huitema |
| 5,762,603 A | 6/1998 | Thompson |
| 5,779,130 A | 7/1998 | Alesi et al. |
| 5,782,396 A | 7/1998 | Mastri et al. |
| 5,782,397 A | 7/1998 | Koukline |
| 5,792,573 A | 8/1998 | Pitzen et al. |
| 5,797,536 A | 8/1998 | Smith et al. |
| 5,820,009 A | 10/1998 | Melling et al. |
| 5,863,159 A | 1/1999 | Lasko |
| 5,908,427 A | 6/1999 | McKean et al. |
| 5,954,259 A | 9/1999 | Viola et al. |
| 5,964,774 A | 10/1999 | McKean et al. |
| 5,993,454 A | 11/1999 | Longo |
| 6,010,054 A | 1/2000 | Johnson et al. |
| 6,017,354 A | 1/2000 | Culp et al. |
| 6,032,849 A | 3/2000 | Mastri et al. |
| 6,045,560 A | 4/2000 | McKean et al. |
| 6,090,123 A | 7/2000 | Culp et al. |
| 6,126,651 A | 10/2000 | Mayer |
| 6,129,547 A | 10/2000 | Cise et al. |
| 6,165,169 A | 12/2000 | Panescu et al. |
| 6,239,732 B1 | 5/2001 | Cusey |
| 6,241,139 B1 | 6/2001 | Milliman et al. |
| 6,264,086 B1 | 7/2001 | McGuckin, Jr. |
| 6,264,087 B1 | 7/2001 | Whitman |
| 6,302,311 B1 | 10/2001 | Adams et al. |
| 6,315,184 B1 | 11/2001 | Whitman |
| 6,321,855 B1 | 11/2001 | Barnes |
| 6,329,778 B1 | 12/2001 | Culp et al. |
| 6,343,731 B1 | 2/2002 | Adams et al. |
| 6,348,061 B1 | 2/2002 | Whitman |
| 6,368,324 B1 | 4/2002 | Dinger et al. |
| 6,371,909 B1 | 4/2002 | Hoeg et al. |
| 6,434,507 B1 | 8/2002 | Clayton et al. |
| 6,443,973 B1 | 9/2002 | Whitman |
| 6,461,372 B1 | 10/2002 | Jensen et al. |
| 6,488,197 B1 | 12/2002 | Whitman |
| 6,491,201 B1 | 12/2002 | Whitman |
| 6,533,157 B1 | 3/2003 | Whitman |
| 6,537,280 B2 | 3/2003 | Dinger et al. |
| 6,610,066 B2 | 8/2003 | Dinger et al. |
| 6,611,793 B1 | 8/2003 | Burnside et al. |
| 6,645,218 B1 | 11/2003 | Cassidy et al. |
| 6,654,999 B2 | 12/2003 | Stoddard et al. |
| 6,698,643 B2 | 3/2004 | Whitman |
| 6,699,177 B1 | 3/2004 | Wang et al. |
| 6,716,233 B1 | 4/2004 | Whitman |
| 6,743,240 B2 | 6/2004 | Smith et al. |
| 6,783,533 B2 | 8/2004 | Green et al. |
| 6,792,390 B1 | 9/2004 | Burnside et al. |
| 6,793,652 B1 | 9/2004 | Whitman et al. |
| 6,817,508 B1 | 11/2004 | Racenet et al. |
| 6,830,174 B2 | 12/2004 | Hillstead et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| 6,860,892 B1 | 3/2005 | Tanaka et al. |
| 6,899,538 B2 | 5/2005 | Matoba |
| 6,905,057 B2 | 6/2005 | Swayze et al. |
| 6,959,852 B2 | 11/2005 | Shelton, IV et al. |
| 6,964,363 B2 | 11/2005 | Wales et al. |
| 6,981,628 B2 | 1/2006 | Wales |
| 6,981,941 B2 | 1/2006 | Whitman et al. |
| 6,986,451 B1 | 1/2006 | Mastri et al. |
| 6,988,649 B2 | 1/2006 | Shelton, IV et al. |
| 7,032,798 B2 | 4/2006 | Whitman et al. |
| RE39,152 E | 6/2006 | Aust et al. |
| 7,055,731 B2 | 6/2006 | Shelton, IV et al. |
| 7,059,508 B2 | 6/2006 | Shelton, IV et al. |
| 7,077,856 B2 | 7/2006 | Whitman |
| 7,111,769 B2 | 9/2006 | Wales et al. |
| 7,122,029 B2 | 10/2006 | Koop et al. |
| 7,140,528 B2 | 11/2006 | Shelton, IV |
| 7,141,049 B2 | 11/2006 | Stern et al. |
| 7,143,923 B2 | 12/2006 | Shelton, IV et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,172,104 B2 | 2/2007 | Scirica et al. |
| 7,225,964 B2 | 6/2007 | Mastri et al. |
| 7,238,021 B1 | 7/2007 | Johnson |
| 7,246,734 B2 | 7/2007 | Shelton, IV |
| 7,252,660 B2 | 8/2007 | Kunz |
| 7,328,828 B2 | 2/2008 | Ortiz et al. |
| 7,364,061 B2 | 4/2008 | Swayze et al. |
| 7,380,695 B2 | 6/2008 | Doll et al. |
| 7,380,696 B2 | 6/2008 | Shelton, IV et al. |
| 7,404,508 B2 | 7/2008 | Smith et al. |
| 7,407,078 B2 | 8/2008 | Shelton, IV et al. |
| 7,416,101 B2 | 8/2008 | Shelton, IV et al. |
| 7,419,080 B2 | 9/2008 | Smith et al. |
| 7,422,139 B2 | 9/2008 | Shelton, IV et al. |
| 7,431,189 B2 | 10/2008 | Shelton, IV et al. |
| 7,441,684 B2 | 10/2008 | Shelton, IV et al. |
| 7,448,525 B2 | 11/2008 | Shelton, IV et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,481,347 B2 | 1/2009 | Roy |
| 7,481,824 B2 | 1/2009 | Boudreaux et al. |
| 7,487,899 B2 | 2/2009 | Shelton, IV et al. |
| 7,549,564 B2 | 6/2009 | Boudreaux |
| 7,565,993 B2 | 7/2009 | Milliman et al. |
| 7,568,603 B2 | 8/2009 | Shelton, IV et al. |
| 7,575,144 B2 | 8/2009 | Ortiz et al. |
| 7,588,175 B2 | 9/2009 | Timm et al. |
| 7,588,176 B2 | 9/2009 | Timm et al. |
| 7,637,409 B2 | 12/2009 | Marczyk |
| 7,641,093 B2 | 1/2010 | Doll et al. |
| 7,644,848 B2 | 1/2010 | Swayze et al. |
| 7,670,334 B2 | 3/2010 | Hueil et al. |
| 7,673,780 B2 | 3/2010 | Shelton, IV et al. |
| 7,699,835 B2 | 4/2010 | Lee et al. |

(56) References Cited

U.S. PATENT DOCUMENTS

| | | | |
|---|---|---|---|
| 7,721,931 | B2 | 5/2010 | Shelton, IV et al. |
| 7,738,971 | B2 | 6/2010 | Swayze et al. |
| 7,740,159 | B2 | 6/2010 | Shelton, IV et al. |
| 7,743,960 | B2 | 6/2010 | Whitman et al. |
| 7,758,613 | B2 | 7/2010 | Whitman |
| 7,766,210 | B2 | 8/2010 | Shelton, IV et al. |
| 7,770,773 | B2 | 8/2010 | Whitman et al. |
| 7,770,775 | B2 | 8/2010 | Shelton, IV et al. |
| 7,793,812 | B2 | 9/2010 | Moore et al. |
| 7,799,039 | B2 | 9/2010 | Shelton, IV et al. |
| 7,802,712 | B2 | 9/2010 | Milliman et al. |
| 7,803,151 | B2 | 9/2010 | Whitman |
| 7,822,458 | B2 | 10/2010 | Webster, III et al. |
| 7,845,534 | B2 | 12/2010 | Viola et al. |
| 7,845,537 | B2 | 12/2010 | Shelton, IV et al. |
| 7,857,185 | B2 | 12/2010 | Swayze et al. |
| 7,870,989 | B2 | 1/2011 | Viola et al. |
| 7,900,805 | B2 | 3/2011 | Shelton, IV et al. |
| 7,905,897 | B2 | 3/2011 | Whitman et al. |
| 7,918,230 | B2 | 4/2011 | Whitman et al. |
| 7,922,061 | B2 | 4/2011 | Shelton, IV et al. |
| 7,922,719 | B2 | 4/2011 | Ralph et al. |
| 7,947,034 | B2 | 5/2011 | Whitman |
| 7,951,071 | B2 | 5/2011 | Whitman et al. |
| 7,954,682 | B2 | 6/2011 | Giordano et al. |
| 7,959,051 | B2 | 6/2011 | Smith et al. |
| 7,963,433 | B2 | 6/2011 | Whitman et al. |
| 7,967,178 | B2 | 6/2011 | Scirica et al. |
| 7,967,179 | B2 | 6/2011 | Olson et al. |
| 7,992,758 | B2 | 8/2011 | Whitman et al. |
| 8,011,550 | B2 | 9/2011 | Aranyi et al. |
| 8,016,178 | B2 | 9/2011 | Olson et al. |
| 8,016,855 | B2 | 9/2011 | Whitman et al. |
| 8,020,743 | B2 | 9/2011 | Shelton, IV |
| 8,025,199 | B2 | 9/2011 | Whitman et al. |
| 8,035,487 | B2 | 10/2011 | Malackowski |
| 8,052,024 | B2 | 11/2011 | Viola et al. |
| 8,114,118 | B2 | 2/2012 | Knodel et al. |
| 8,127,975 | B2 | 3/2012 | Olson et al. |
| 8,132,705 | B2 | 3/2012 | Viola et al. |
| 8,152,516 | B2 | 4/2012 | Harvey et al. |
| 8,157,150 | B2 | 4/2012 | Viola et al. |
| 8,157,151 | B2 | 4/2012 | Ingmanson et al. |
| 8,182,494 | B1 | 5/2012 | Yencho et al. |
| 8,186,555 | B2 | 5/2012 | Shelton, IV et al. |
| 8,186,587 | B2 | 5/2012 | Zmood et al. |
| 8,220,367 | B2 | 7/2012 | Hsu |
| 8,235,273 | B2 | 8/2012 | Olson et al. |
| 8,241,322 | B2 | 8/2012 | Whitman et al. |
| 8,272,554 | B2 | 9/2012 | Whitman et al. |
| 8,292,150 | B2 | 10/2012 | Bryant |
| 8,292,888 | B2 | 10/2012 | Whitman |
| 8,342,379 | B2 | 1/2013 | Whitman et al. |
| 8,348,130 | B2 | 1/2013 | Shah et al. |
| 8,348,855 | B2 | 1/2013 | Hillely et al. |
| 8,353,440 | B2 | 1/2013 | Whitman et al. |
| 8,357,144 | B2 | 1/2013 | Whitman et al. |
| 8,365,633 | B2 | 2/2013 | Simaan et al. |
| 8,365,972 | B2 | 2/2013 | Aranyi et al. |
| 8,371,492 | B2 | 2/2013 | Aranyi et al. |
| 8,372,057 | B2 | 2/2013 | Cude et al. |
| 8,391,957 | B2 | 3/2013 | Carlson et al. |
| 8,403,926 | B2 | 3/2013 | Nobis et al. |
| 8,418,904 | B2 | 4/2013 | Wenchell et al. |
| 8,424,739 | B2 | 4/2013 | Racenet et al. |
| 8,454,585 | B2 | 6/2013 | Whitman |
| 8,505,802 | B2 | 8/2013 | Viola et al. |
| 8,517,241 | B2 | 8/2013 | Nicholas et al. |
| 8,523,043 | B2 | 9/2013 | Ullrich et al. |
| 8,551,076 | B2 | 10/2013 | Duval et al. |
| 8,561,871 | B2 | 10/2013 | Rajappa et al. |
| 8,561,874 | B2 | 10/2013 | Scirica |
| 8,602,287 | B2 | 12/2013 | Yates et al. |
| 8,623,000 | B2 | 1/2014 | Humayun et al. |
| 8,627,995 | B2 | 1/2014 | Smith et al. |
| 8,632,463 | B2 | 1/2014 | Drinan et al. |
| 8,636,766 | B2 | 1/2014 | Milliman et al. |
| 8,647,258 | B2 | 2/2014 | Aranyi et al. |
| 8,652,121 | B2 | 2/2014 | Quick et al. |
| 8,657,174 | B2 | 2/2014 | Yates et al. |
| 8,657,177 | B2 | 2/2014 | Scirica et al. |
| 8,672,206 | B2 | 3/2014 | Aranyi et al. |
| 8,696,552 | B2 | 4/2014 | Whitman |
| 8,708,213 | B2 | 4/2014 | Shelton, IV et al. |
| 8,715,306 | B2 | 5/2014 | Faller et al. |
| 8,758,391 | B2 | 6/2014 | Swayze et al. |
| 8,806,973 | B2 | 8/2014 | Ross et al. |
| 8,808,311 | B2 | 8/2014 | Heinrich et al. |
| 8,820,605 | B2 | 9/2014 | Shelton, IV |
| 8,851,355 | B2 | 10/2014 | Aranyi et al. |
| 8,858,571 | B2 | 10/2014 | Shelton, IV et al. |
| 8,875,972 | B2 | 11/2014 | Weisenburgh, II et al. |
| 8,888,762 | B2 | 11/2014 | Whitman |
| 8,893,946 | B2 | 11/2014 | Boudreaux et al. |
| 8,899,462 | B2 | 12/2014 | Kostrzewski et al. |
| 8,905,289 | B2 | 12/2014 | Patel et al. |
| 8,919,630 | B2 | 12/2014 | Milliman |
| 8,931,680 | B2 | 1/2015 | Milliman |
| 8,939,344 | B2 | 1/2015 | Olson et al. |
| 8,950,646 | B2 | 2/2015 | Viola |
| 8,960,519 | B2 | 2/2015 | Whitman et al. |
| 8,961,396 | B2 | 2/2015 | Azarbarzin et al. |
| 8,967,443 | B2 | 3/2015 | McCuen |
| 8,968,276 | B2 | 3/2015 | Zemlok et al. |
| 8,968,337 | B2 | 3/2015 | Whitfield et al. |
| 8,992,422 | B2 | 3/2015 | Spivey et al. |
| 9,016,545 | B2 | 4/2015 | Aranyi et al. |
| 9,023,014 | B2 | 5/2015 | Chowaniec et al. |
| 9,033,868 | B2 | 5/2015 | Whitman et al. |
| 9,055,943 | B2 | 6/2015 | Zemlok et al. |
| 9,064,653 | B2 | 6/2015 | Prest et al. |
| 9,072,515 | B2 | 7/2015 | Hall et al. |
| 9,113,847 | B2 | 8/2015 | Whitman et al. |
| 9,113,875 | B2 | 8/2015 | Viola et al. |
| 9,113,876 | B2 | 8/2015 | Zemlok et al. |
| 9,113,899 | B2 | 8/2015 | Garrison et al. |
| 9,216,013 | B2 | 12/2015 | Scirica et al. |
| 9,241,712 | B2 | 1/2016 | Zemlok et al. |
| 9,282,961 | B2 | 3/2016 | Whitman et al. |
| 9,282,963 | B2 | 3/2016 | Bryant |
| 9,295,522 | B2 | 3/2016 | Kostrzewski |
| 9,307,986 | B2 | 4/2016 | Hall et al. |
| 10,973,544 | B2 * | 4/2021 | Williams .......... A61B 17/1155 |
| 2001/0031975 | A1 | 10/2001 | Whitman et al. |
| 2002/0049454 | A1 | 4/2002 | Whitman et al. |
| 2002/0165541 | A1 | 11/2002 | Whitman |
| 2003/0038938 | A1 | 2/2003 | Jung et al. |
| 2003/0165794 | A1 | 9/2003 | Matoba |
| 2004/0034369 | A1 | 2/2004 | Sauer et al. |
| 2004/0111012 | A1 | 6/2004 | Whitman |
| 2004/0133189 | A1 | 7/2004 | Sakurai |
| 2004/0153124 | A1 | 8/2004 | Whitman |
| 2004/0176751 | A1 | 9/2004 | Weitzner et al. |
| 2004/0193146 | A1 | 9/2004 | Lee et al. |
| 2005/0125027 | A1 | 6/2005 | Knodel et al. |
| 2005/0131442 | A1 | 6/2005 | Yachia et al. |
| 2006/0142656 | A1 | 6/2006 | Malackowski et al. |
| 2006/0142740 | A1 | 6/2006 | Sherman et al. |
| 2006/0142744 | A1 | 6/2006 | Boutoussov |
| 2006/0259073 | A1 | 11/2006 | Miyamoto et al. |
| 2006/0278680 | A1 | 12/2006 | Viola et al. |
| 2006/0284730 | A1 | 12/2006 | Schmid et al. |
| 2007/0023476 | A1 | 2/2007 | Whitman et al. |
| 2007/0023477 | A1 | 2/2007 | Whitman et al. |
| 2007/0027469 | A1 | 2/2007 | Smith et al. |
| 2007/0029363 | A1 | 2/2007 | Popov |
| 2007/0084897 | A1 | 4/2007 | Shelton et al. |
| 2007/0102472 | A1 | 5/2007 | Shelton |
| 2007/0152014 | A1 | 7/2007 | Gillum et al. |
| 2007/0175947 | A1 | 8/2007 | Ortiz et al. |
| 2007/0175949 | A1 | 8/2007 | Shelton et al. |
| 2007/0175950 | A1 | 8/2007 | Shelton et al. |
| 2007/0175951 | A1 | 8/2007 | Shelton et al. |
| 2007/0175955 | A1 | 8/2007 | Shelton et al. |

(56) References Cited

U.S. PATENT DOCUMENTS

| | | |
|---|---|---|
| 2007/0270784 A1 | 11/2007 | Smith et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0058801 A1 | 3/2008 | Taylor et al. |
| 2008/0109012 A1 | 5/2008 | Falco et al. |
| 2008/0110958 A1 | 5/2008 | McKenna et al. |
| 2008/0147089 A1 | 6/2008 | Loh et al. |
| 2008/0167736 A1 | 7/2008 | Swayze et al. |
| 2008/0185419 A1 | 8/2008 | Smith et al. |
| 2008/0188841 A1 | 8/2008 | Tomasello et al. |
| 2008/0197167 A1 | 8/2008 | Viola et al. |
| 2008/0208195 A1 | 8/2008 | Shores et al. |
| 2008/0237296 A1 | 10/2008 | Boudreaux et al. |
| 2008/0251561 A1 | 10/2008 | Eades et al. |
| 2008/0255413 A1 | 10/2008 | Zemlok et al. |
| 2008/0255607 A1 | 10/2008 | Zemlok |
| 2008/0262654 A1 | 10/2008 | Omori et al. |
| 2008/0308603 A1 | 12/2008 | Shelton et al. |
| 2009/0012533 A1 | 1/2009 | Barbagli et al. |
| 2009/0090763 A1 | 4/2009 | Zemlok et al. |
| 2009/0099876 A1 | 4/2009 | Whitman |
| 2009/0138006 A1 | 5/2009 | Bales et al. |
| 2009/0171147 A1 | 7/2009 | Lee et al. |
| 2009/0182193 A1 | 7/2009 | Whitman et al. |
| 2009/0209946 A1 | 8/2009 | Swayze et al. |
| 2009/0209990 A1 | 8/2009 | Yates et al. |
| 2009/0254094 A1 | 10/2009 | Knapp et al. |
| 2009/0299141 A1 | 12/2009 | Downey et al. |
| 2010/0023022 A1 | 1/2010 | Zeiner et al. |
| 2010/0069942 A1 | 3/2010 | Shelton, IV |
| 2010/0193568 A1 | 8/2010 | Scheib et al. |
| 2010/0211053 A1 | 8/2010 | Ross et al. |
| 2010/0225073 A1 | 9/2010 | Porter et al. |
| 2011/0071508 A1 | 3/2011 | Duval et al. |
| 2011/0077673 A1 | 3/2011 | Grubac et al. |
| 2011/0121049 A1 | 5/2011 | Malinouskas et al. |
| 2011/0125138 A1 | 5/2011 | Malinouskas et al. |
| 2011/0139851 A1 | 6/2011 | McCuen |
| 2011/0155783 A1 | 6/2011 | Rajappa et al. |
| 2011/0155786 A1 | 6/2011 | Shelton, IV |
| 2011/0172648 A1 | 7/2011 | Jeong |
| 2011/0174009 A1 | 7/2011 | Iizuka et al. |
| 2011/0174099 A1 | 7/2011 | Ross et al. |
| 2011/0184245 A1 | 7/2011 | Xia et al. |
| 2011/0204119 A1 | 8/2011 | McCuen |
| 2011/0218522 A1 | 9/2011 | Whitman |
| 2011/0276057 A1 | 11/2011 | Conlon et al. |
| 2011/0290854 A1 | 12/2011 | Timm et al. |
| 2011/0295242 A1 | 12/2011 | Spivey et al. |
| 2011/0295269 A1 | 12/2011 | Swensgard et al. |
| 2012/0000962 A1 | 1/2012 | Racenet et al. |
| 2012/0074199 A1 | 3/2012 | Olson et al. |
| 2012/0089131 A1 | 4/2012 | Zemlok et al. |
| 2012/0104071 A1 | 5/2012 | Bryant |
| 2012/0116368 A1 | 5/2012 | Viola |
| 2012/0143002 A1 | 6/2012 | Aranyi et al. |
| 2012/0172924 A1 | 7/2012 | Allen, IV |
| 2012/0211542 A1 | 8/2012 | Racenet |
| 2012/0223121 A1 | 9/2012 | Viola et al. |
| 2012/0245428 A1 | 9/2012 | Smith et al. |
| 2012/0253329 A1 | 10/2012 | Zemlok et al. |
| 2012/0310220 A1 | 12/2012 | Malkowski et al. |
| 2012/0323226 A1 | 12/2012 | Chowaniec et al. |
| 2012/0330285 A1 | 12/2012 | Hartoumbekis et al. |
| 2013/0093149 A1 | 4/2013 | Saur et al. |
| 2013/0181035 A1 | 7/2013 | Milliman |
| 2013/0184704 A1 | 7/2013 | Beardsley et al. |
| 2013/0214025 A1 | 8/2013 | Zemlok et al. |
| 2013/0274722 A1 | 10/2013 | Kostrzewski et al. |
| 2013/0282052 A1 | 10/2013 | Aranyi et al. |
| 2013/0292451 A1 | 11/2013 | Viola et al. |
| 2013/0313304 A1 | 11/2013 | Shelton, IV et al. |
| 2013/0317486 A1 | 11/2013 | Nicholas et al. |
| 2013/0319706 A1 | 12/2013 | Nicholas et al. |
| 2013/0324978 A1 | 12/2013 | Nicholas et al. |
| 2013/0324979 A1 | 12/2013 | Nicholas et al. |
| 2013/0334281 A1 | 12/2013 | Williams |
| 2014/0012236 A1 | 1/2014 | Williams et al. |
| 2014/0012237 A1 | 1/2014 | Pribanic et al. |
| 2014/0012289 A1 | 1/2014 | Snow et al. |
| 2014/0025046 A1 | 1/2014 | Williams et al. |
| 2014/0110455 A1 | 4/2014 | Ingmanson et al. |
| 2014/0207125 A1 | 7/2014 | Applegate et al. |
| 2014/0207182 A1 | 7/2014 | Zergiebel et al. |
| 2014/0207185 A1 | 7/2014 | Goble et al. |
| 2014/0236174 A1 | 8/2014 | Williams et al. |
| 2014/0276932 A1 | 9/2014 | Williams et al. |
| 2014/0299647 A1 | 10/2014 | Scirica et al. |
| 2014/0303668 A1 | 10/2014 | Nicholas et al. |
| 2014/0358129 A1 | 12/2014 | Zergiebel et al. |
| 2014/0361068 A1 | 12/2014 | Aranyi et al. |
| 2014/0365235 A1 | 12/2014 | DeBoer et al. |
| 2014/0373652 A1 | 12/2014 | Zergiebel et al. |
| 2015/0014392 A1 | 1/2015 | Williams et al. |
| 2015/0048144 A1 | 2/2015 | Whitman |
| 2015/0076205 A1 | 3/2015 | Zergiebel |
| 2015/0080912 A1 | 3/2015 | Sapre |
| 2015/0112381 A1 | 4/2015 | Richard |
| 2015/0122870 A1 | 5/2015 | Zemlok et al. |
| 2015/0133224 A1 | 5/2015 | Whitman et al. |
| 2015/0150547 A1 | 6/2015 | Ingmanson et al. |
| 2015/0150574 A1 | 6/2015 | Richard et al. |
| 2015/0157320 A1 | 6/2015 | Zergiebel et al. |
| 2015/0157321 A1 | 6/2015 | Zergiebel et al. |
| 2015/0164502 A1 | 6/2015 | Richard et al. |
| 2015/0201931 A1 | 7/2015 | Zergiebel et al. |
| 2015/0272577 A1 | 10/2015 | Zemlok et al. |
| 2015/0297199 A1 | 10/2015 | Nicholas et al. |
| 2015/0303996 A1 | 10/2015 | Calderoni |
| 2015/0320420 A1 | 11/2015 | Penna et al. |
| 2015/0327850 A1 | 11/2015 | Kostrzewski |
| 2015/0342601 A1 | 12/2015 | Williams et al. |
| 2015/0342603 A1 | 12/2015 | Zergiebel et al. |
| 2015/0374366 A1 | 12/2015 | Zergiebel et al. |
| 2015/0374370 A1 | 12/2015 | Zergiebel et al. |
| 2015/0374371 A1 | 12/2015 | Richard et al. |
| 2015/0374372 A1 | 12/2015 | Zergiebel et al. |
| 2015/0374449 A1 | 12/2015 | Chowaniec et al. |
| 2015/0380187 A1 | 12/2015 | Zergiebel et al. |
| 2016/0095585 A1 | 4/2016 | Zergiebel et al. |
| 2016/0095596 A1 | 4/2016 | Scirica et al. |
| 2016/0106406 A1 | 4/2016 | Cabrera et al. |
| 2016/0113648 A1 | 4/2016 | Zergiebel et al. |
| 2016/0113649 A1 | 4/2016 | Zergiebel et al. |
| 2017/0086879 A1* | 3/2017 | Williams .......... A61B 17/3417 |
| 2017/0196566 A1* | 7/2017 | Sgroi ................ A61B 17/1155 |
| 2017/0333077 A1* | 11/2017 | Williams .......... A61B 17/07207 |
| 2018/0280024 A1* | 10/2018 | Williams ............. A61B 17/068 |

FOREIGN PATENT DOCUMENTS

| | | |
|---|---|---|
| CN | 1957854 A | 5/2007 |
| CN | 101495046 A | 7/2009 |
| CN | 102247182 A | 11/2011 |
| DE | 202008009527 U1 | 10/2008 |
| DE | 102008053842 A1 | 5/2010 |
| EP | 0705571 | 4/1996 |
| EP | 1563793 A1 | 8/2005 |
| EP | 1769754 A1 | 4/2007 |
| EP | 2316345 A1 | 5/2011 |
| EP | 2668910 A2 | 12/2013 |
| EP | 3245959 A2 | 11/2017 |
| EP | 3412225 A1 | 12/2018 |
| ES | 2333509 A1 | 2/2010 |
| JP | 2005125075 A | 5/2005 |
| KR | 20120022521 A | 3/2012 |
| WO | 2011108840 A2 | 9/2011 |
| WO | 2012/040984 A1 | 4/2012 |

\* cited by examiner

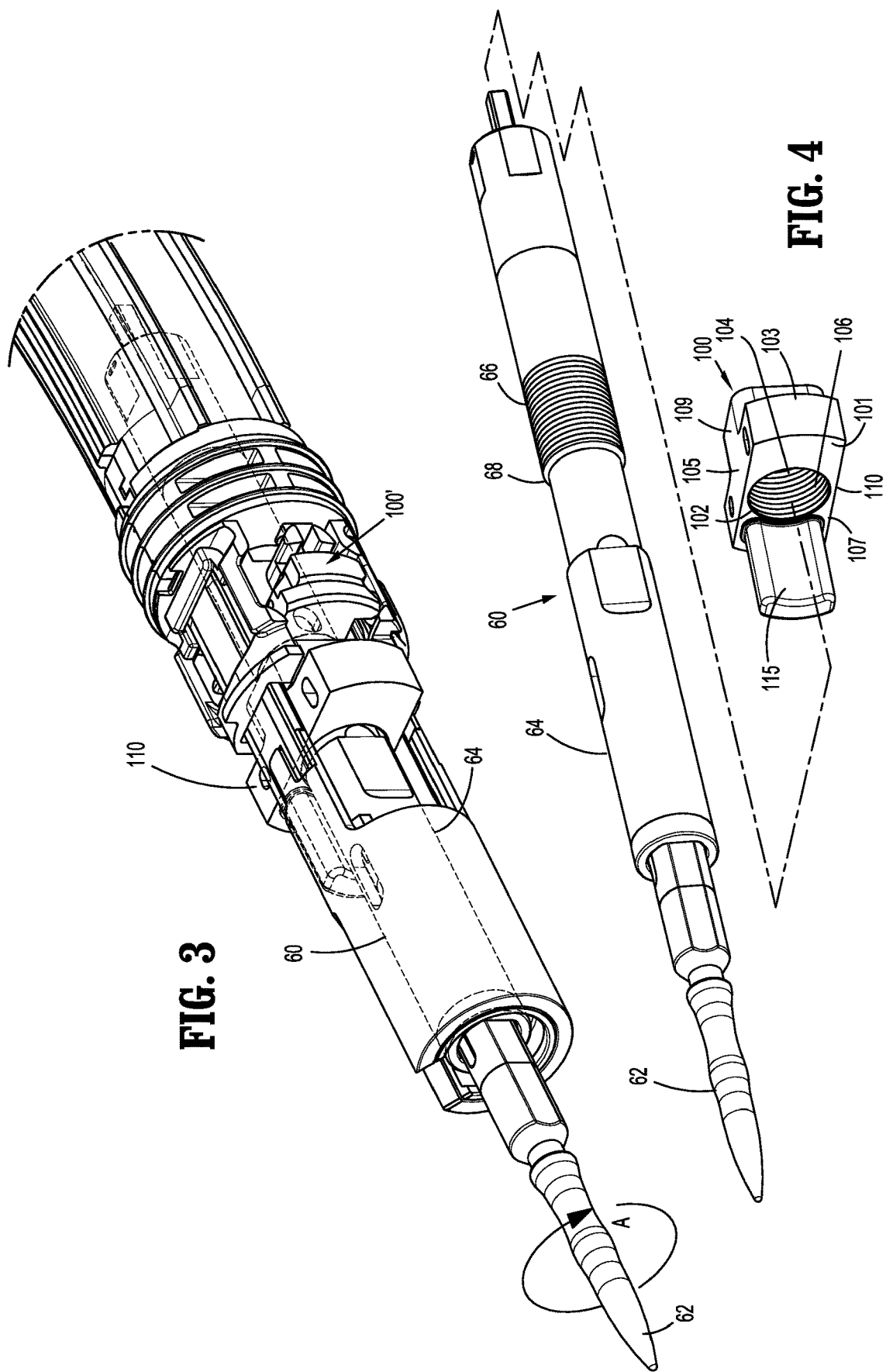

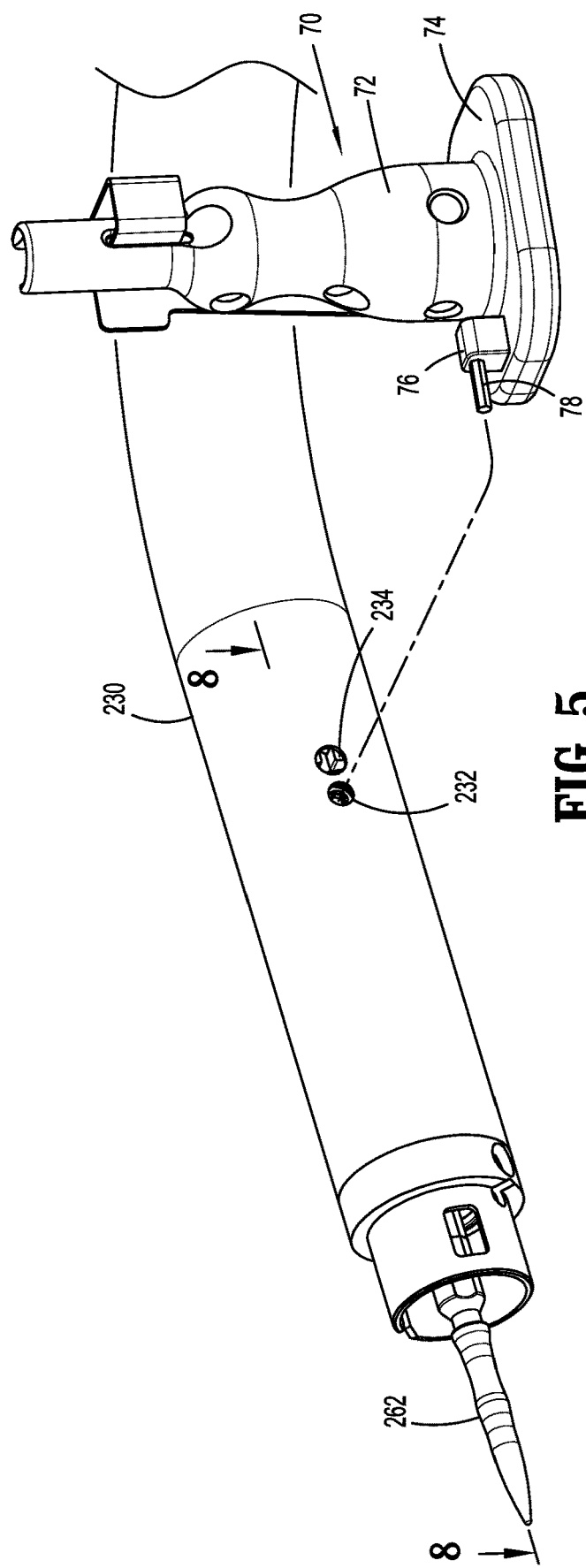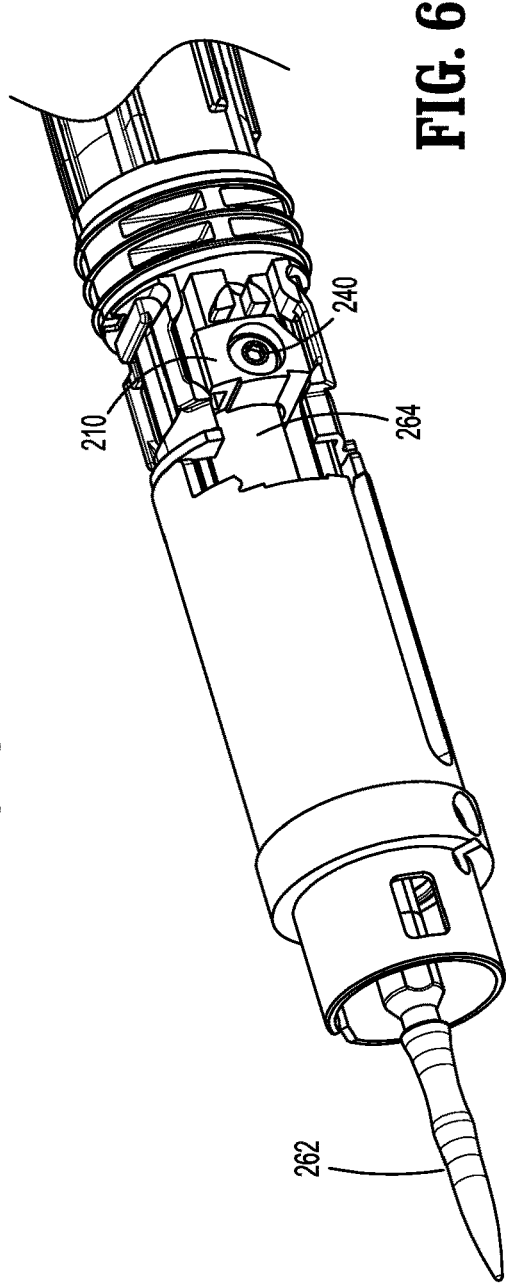

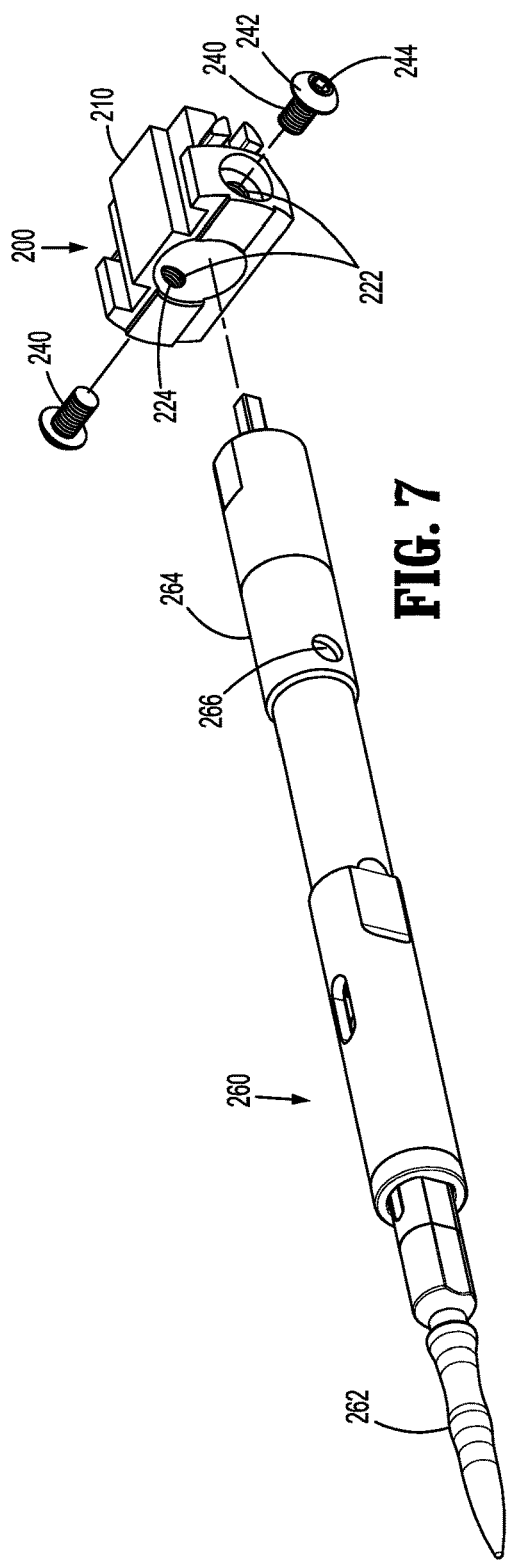
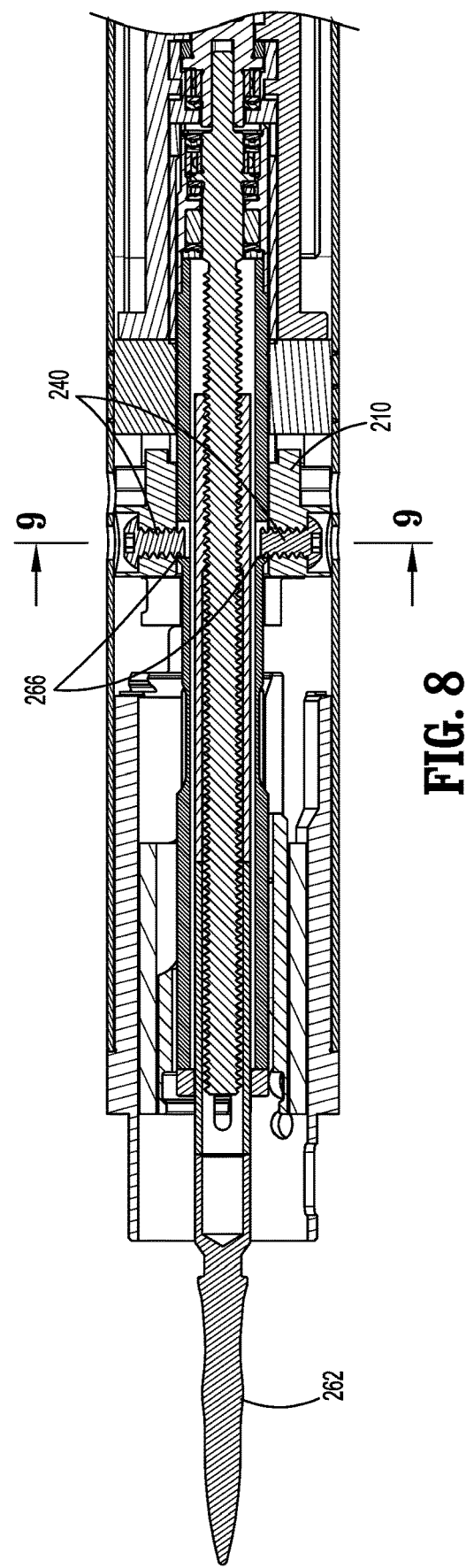
FIG. 7
FIG. 8

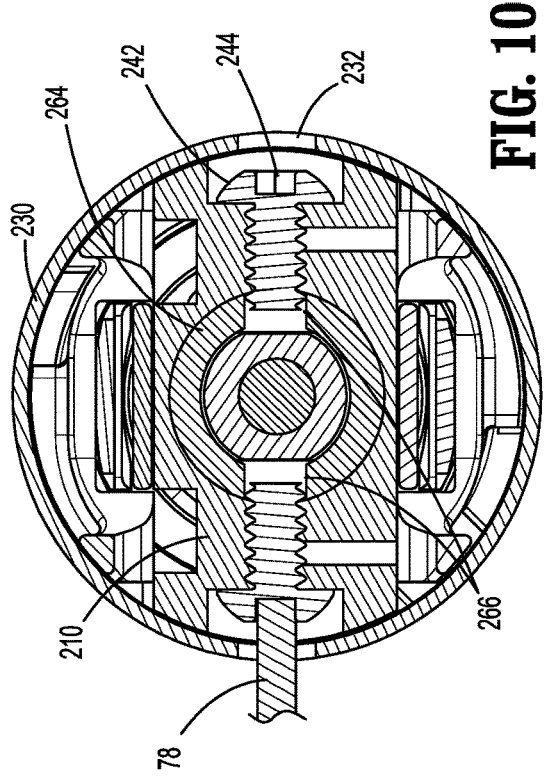
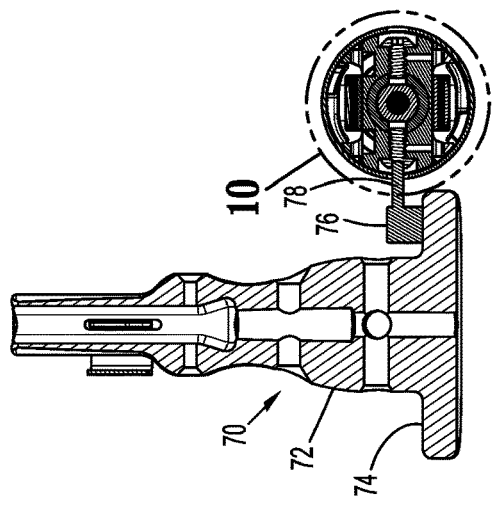
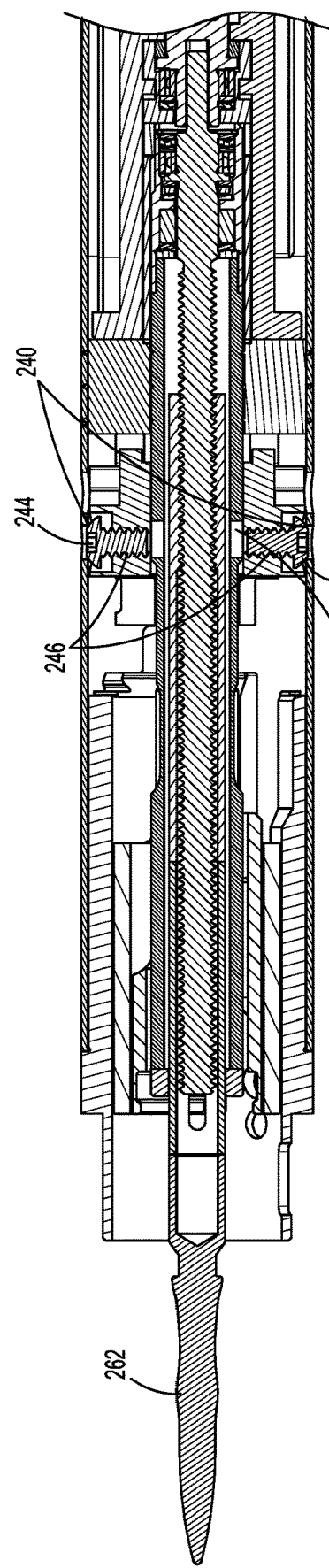
FIG. 10
FIG. 11
FIG. 9

TROCAR COUPLING ASSEMBLIES FOR A SURGICAL STAPLER

FIELD

The present disclosure relates generally to assemblies for coupling a trocar assembly to a surgical stapler. More particularly, the present disclosure relates to assemblies for securely coupling a trocar assembly partially within an elongated body portion of a surgical stapler.

BACKGROUND

Anastomosis is the surgical joining of separate hollow organ sections. Typically, an anastomosis procedure follows surgery in which a diseased or defective section of hollow tissue is removed, and the end sections are stapled via a surgical stapler. Depending on the desired anastomosis procedure, the end sections may be joined by circular or side-to-side organ reconstruction methods, for instance.

In a circular anastomosis procedure, the two ends of the organ sections are joined by means of a surgical stapler which drives a circular array of staples through the end section of each organ section and simultaneously cores any tissue interior of the driven circular array of staples to free the tubular passage. Typically, these surgical staplers include an elongated body portion having a handle portion at a proximal end to actuate the surgical stapler and a staple holding component disposed at a distal end. An anvil assembly including an anvil retention rod with an attached anvil head is mounted to a trocar assembly at the distal end of the surgical stapler adjacent the staple-holding component. Opposed end portions of tissue of the hollow organ(s) to be stapled are clamped between the anvil head and the staple holding component. The clamped tissue is stapled by driving one or more staples from the staple holding component so that the ends of the staples pass through the tissue and are deformed by the anvil head. An annular knife is advanced to core tissue within the hollow organ to free a tubular passage within the organ.

Besides anastomosis of hollow organs, surgical staplers for performing circular anastomosis have been used to treat internal hemorrhoids in the rectum. Typically, during use of a surgical stapler for hemorrhoid treatment, the anvil head and the staple holding-component of the surgical stapler are inserted through the anus and into the rectum with the anvil head and the staple-holding component in an open or unapproximated position. Thereafter, a purse string suture is used to pull the internal hemorrhoidal tissue towards the anvil rod. Next, the anvil head and staple-holding component are approximated to clamp the hemorrhoidal tissue between the anvil head and the staple holding component. During the approximation of the anvil head and the staple-holding component, the trocar assembly engages the anvil retention rod. The surgical stapler is fired to remove the hemorrhoidal tissue and staple the cut tissue.

It may be desirable to select a particular trocar assembly depending on the type of surgical procedure being performed. Further, it may be helpful to remove the trocar assembly after use to facilitate the sanitization thereof, if reusing the trocar assembly is desired, for instance.

SUMMARY

According to an embodiment of the present disclosure, a trocar coupling assembly for a surgical stapler includes a housing having opposed openings defining a passage therethrough and the passage is configured to receive a sleeve of a trocar assembly therein. The trocar coupling assembly also includes a release button, a spring, a retention pin, and a clip. The release button is movably coupled to the housing and movable between a relaxed position and a compressed position. The spring is disposed between the housing and the release button, the spring biasing the release button towards the extended position. The retention pin is disposed in a bore of the housing and slidable between extended and retracted position. The clip operatively couples the release button and the retention pin, the clip translatable between first and second positions, the first position biasing the retention pin towards the extended position and the second position moving the retention pin to the retracted position.

The compressed position of the release button and the retracted position of the retention pin may define an unlocked configuration of the trocar coupling assembly. The locked configuration of the trocar coupling assembly may inhibit insertion of a trocar assembly into the passage of the housing. The relaxed position of the release button and the extended position of the retention pin may define a locked configuration of the trocar coupling assembly.

A sleeve of a trocar assembly may be insertable into the passage of the housing with the trocar coupling assembly in the unlocked configuration.

A distal portion of the retention pin may be engageable with a slot in an outer surface of a sleeve of a trocar assembly to maintain a fixed axial relationship between the trocar coupling assembly and a trocar assembly.

A leg of the clip may extend through a pathway of the retention pin.

A bottom surface of the release button may engage a backspan of the clip.

A backspan of the clip may contact a portion of the spring such that moving the release button towards the compressed position urges the spring and the clip towards a bottom surface of the housing.

The trocar coupling assembly may be positionable within a lumen of a tubular shaft.

The housing may be positionable in a lumen of a tubular shaft and a portion of the retention pin may extend through an orifice of the tubular shaft thereby providing a visual indication that the trocar coupling assembly is in the unlocked configuration.

The housing may include a cutout extending parallel to the passage and intersecting the bore of the housing and the cutout may be configured to receive a portion of a plate.

The plate may be secured to a drive band and inhibited from movement in a distal direction with the trocar release assembly in the unlocked configuration.

An extended position of the retention pin may allow proximal and distal movement of the drive band.

In embodiments, a shaft for use with a surgical stapler includes a tubular member and a trocar coupling assembly positionable in the tubular member. The trocar coupling assembly includes a housing having opposed openings and a passage defined between the opposed openings of the housing, the passage including internal threads. The shaft also includes a trocar assembly having a sleeve with an outer surface, the outer surface including a slot extending therethrough and external threads. The external threads are complimentary to the internal threads of the passage such that rotation of the sleeve relative to the housing translates the trocar assembly axially with respect to the housing. A trocar is disposed in a lumen of the sleeve.

In embodiments, a shaft for use with a surgical stapler includes a tubular member with an opening extending through an outer wall thereof, a housing disposed in the tubular member and having opposed openings along a longitudinal axis thereof, a passage defined between the opposed openings of the housing and configured to slidably receive a trocar assembly therethrough. A bore extends through the housing in an orientation transverse to the passage and is in communication with the opening. A fastener is insertable through the opening and the bore, the fastener including a head and a shaft extending therefrom, the shaft including threads on a portion thereof, a distal portion of the shaft insertable into a retention slot of a sleeve of a trocar assembly to fix an axial position of a trocar assembly with respect to the housing.

BRIEF DESCRIPTION OF DRAWINGS

Embodiments of trocar coupling assemblies for use with a surgical stapler are disclosed herein with reference to the drawings, wherein:

FIG. 3 is an enlarged view of the indicated area of detail of FIG. 2;

FIG. 4 is an exploded perspective view, with parts separated, of the trocar assembly and the load sensor of FIG. 2;

FIG. 5 is a perspective view of a distal region of a tubular shaft and a tool according to a further embodiment of the present disclosure;

FIG. 6 is a perspective view of the distal region of the tubular shaft of FIG. 5 with an outer tube removed;

FIG. 7 is an exploded perspective view, with parts separated, of the trocar coupling assembly of FIG. 6;

FIG. 8 is a side cross-sectional view of the distal region of the tubular shaft of FIG. 5 taken along section line 8-8 of FIG. 5 illustrating a locked configuration of the trocar coupling assembly;

FIG. 9 is an end cross-sectional view of the distal region of the tubular shaft of FIG. 8 taken along section line 9-9 of FIG. 8 showing the tool of FIG. 5 engaged with a screw;

FIG. 10 is an enlarged view of the indicated area of detail of FIG. 9;

FIG. 11 is a side cross-sectional view of the distal region of the tubular shaft of FIG. 8 illustrating an unlocked configuration of the trocar coupling assembly;

DETAILED DESCRIPTION

Embodiments of the presently disclosed trocar coupling assembly for a surgical stapler will now be described in detail with reference to the drawings wherein like numerals designate identical or corresponding elements in each of the several views. As is common in the art, the term "proximal" refers to that part or component closer to the user or operator, i.e. surgeon or physician, while the term "distal" refers to that part or component farther away from the user.

Figure 1:
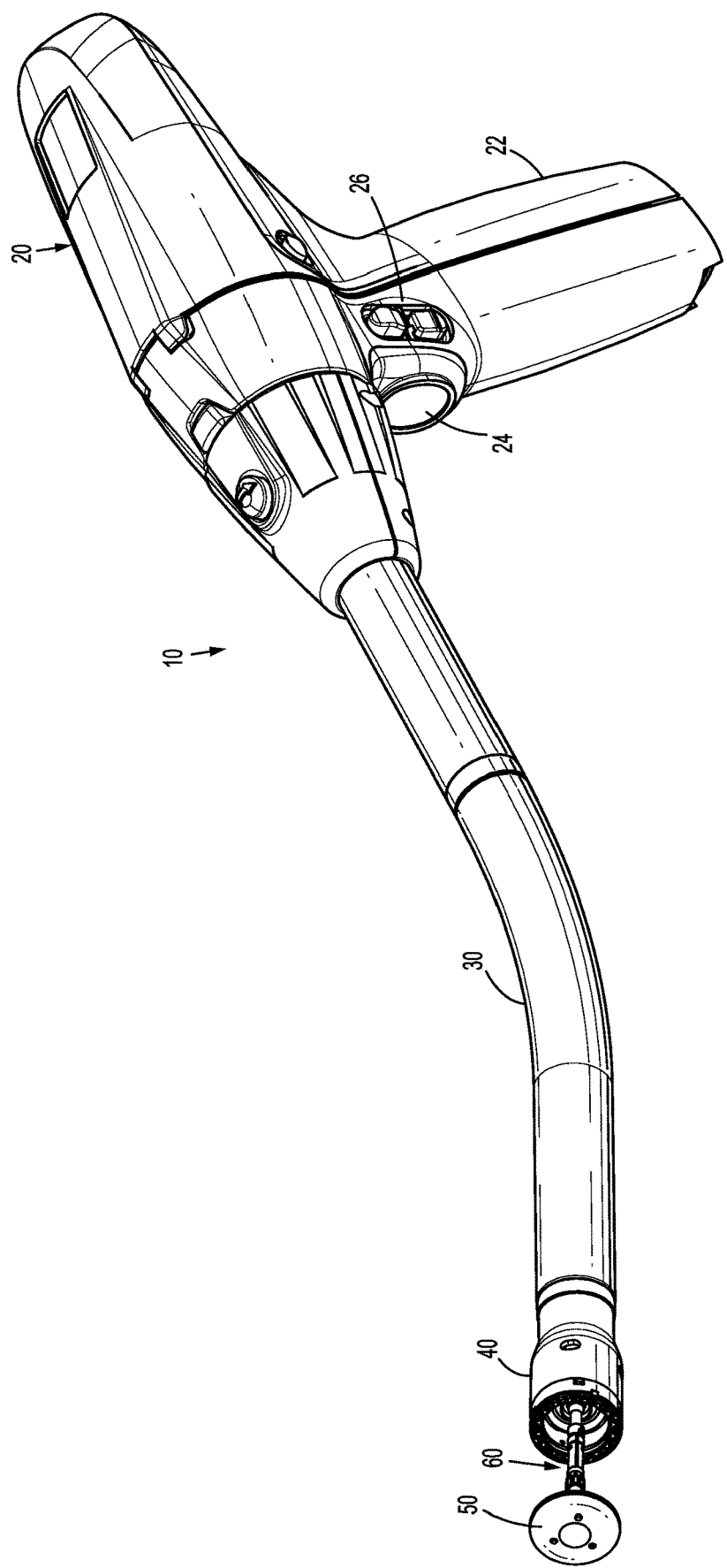
FIG. 1 is a perspective view of a surgical stapler according to an embodiment of the present disclosure.
Figure 2:
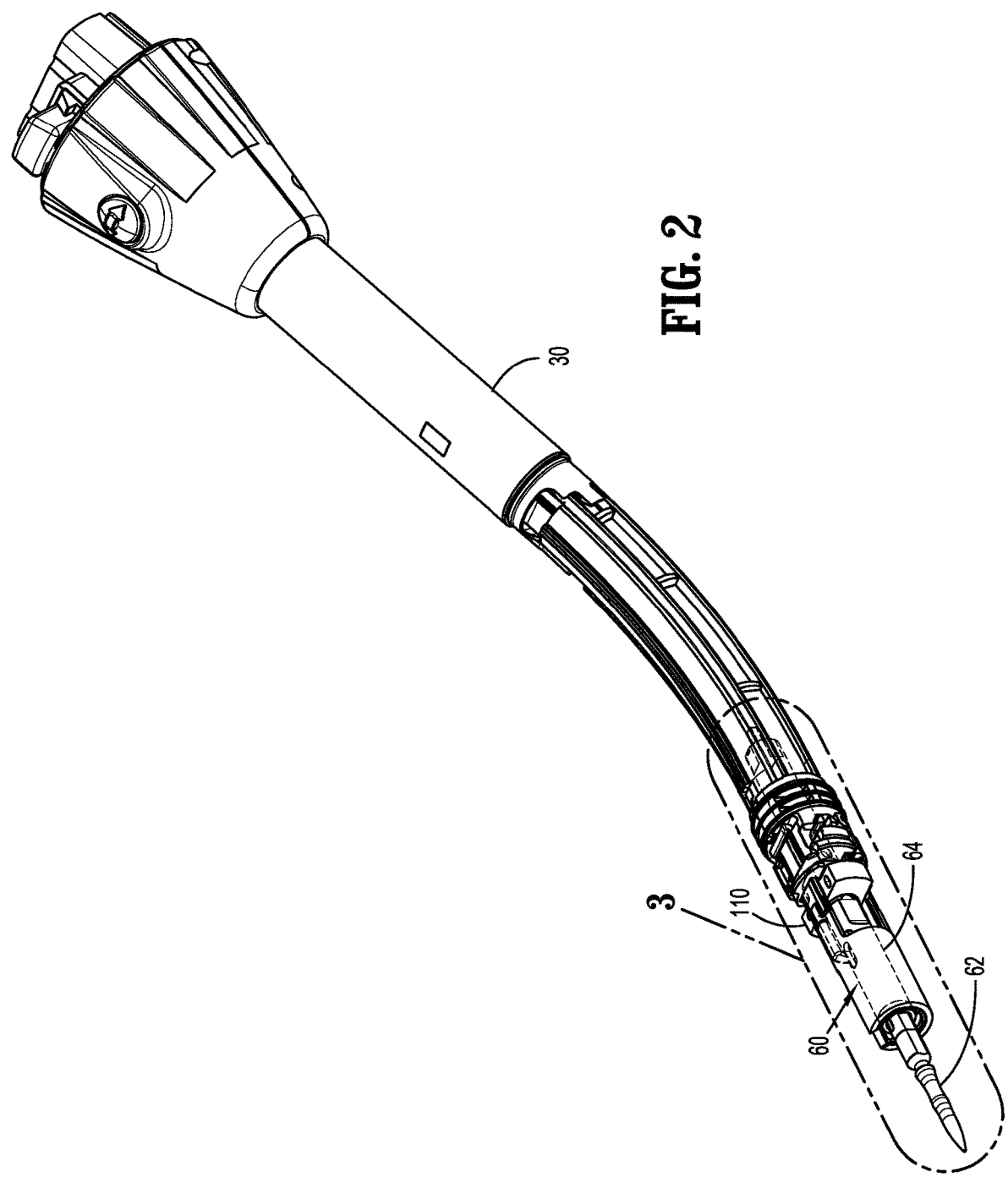
FIG. 2 is a perspective view of a tubular shaft of the surgical stapler of FIG. 1 illustrating an embodiment of a trocar assembly, a trocar coupling assembly, and a load sensor shown in phantom.

Initially, with reference to FIGS. 1 and 2, a surgical stapler is shown and referenced generally as surgical stapler 10. The surgical stapler 10 is a circular stapler and includes a handle 20 assembly at one end and a tubular shaft 30 extending from the handle assembly 20. The tubular shaft 30 includes an open distal end for receiving a trocar assembly 60 therein. Although illustrated as a powered surgical stapler, surgical stapler 10 may be a manually operated instrument. The handle assembly 20 includes a power source (not shown) and buttons for operating the surgical stapler 10. A cartridge 40 is disposed at a distal end of the tubular shaft 30. The handle assembly 20 includes a fixed handle 22, an actuation button 24, and an approximation mechanism 26 for moving the trocar assembly 60 and an anvil 50 relative to the cartridge 40. The structure and function of handle assembly 20 will only be described herein to the extent necessary. It is envisioned that shell assembly may be used with any actuation assembly, powered or manual, and capable of two independent actuation strokes, for example. Commonly owned U.S. Pat. No. 8,806,973, the content of which is incorporated by reference herein in its entirety, discloses a surgical device having a powered actuator assembly including first and second drive members. In addition, it is envisioned that the independent actuation strokes may be completed by the same drive member completing two strokes or by two separate drive members. A trocar coupling assembly 100, as will be described in further detail hereinbelow, is positioned in the tubular shaft 30. The trocar assembly 60 includes a trocar member 62 extending from a sleeve 64.

With additional reference to FIGS. 3 and 4, the load sensor 100 has a housing 110 with a planar end face 101, arcuate side faces 103, planar top and bottom faces 105, 107, and a protrusion 109 extending from a distal portion of the housing 110. The protrusion 109 has an open proximal end (not shown) that in conjunction with open distal end 102 defines a passage 104 therebetween. The passage 104 includes internal threads 106. The sleeve 64 of the trocar assembly 60 includes external threads 66 formed along a portion of an outer surface of the sleeve 64. The external threads 66 are configured to threadably engage the internal threads 106 of the passage 104 located along an inner diameter of the housing 1110. As seen in FIG. 3, rotation of the trocar assembly 60 relative to the housing 110 in the direction of arrow "A" acts to couple the trocar assembly 60 with the housing 110 of the load sensor 100. The trocar assembly 60 is rotated relative to the load sensor 100 such that the external threads 66 engage the internal threads 106 thereby coupling the trocar assembly 60 with the housing 110 of the load sensor 100. Continued relative rotation between the trocar assembly 60 and the housing 110 in the direction of arrow "A" seats the trocar assembly 60 in the housing 110 such that relative linear movement between the trocar assembly 60 and the housing 110 is inhibited and the trocar assembly 60 is securely coupled in the tubular shaft 30 of the surgical stapler 10. The external threads 66 of the trocar assembly 60 may include an enlarged helical ridge 68 at a distal end of the external threads 66. The enlarged helical ridge 68 has a greater outer diameter than the remainder of the external threads 66 and an inner diameter of the internal threads 106 of the housing 110. Thus, the trocar assembly 60 is only threadable into the housing 110 up to the point where the enlarged helical ridge 68 abuts the open distal end 102 and continued relative rotation between the trocar assembly 60 and the housing 110 ceases. The enlarged helical ridge 68 acts as a limit stop defining the maximum insertion depth of the trocar assembly 60 in the housing 110. Conversely, rotation in the direction opposite of arrow "A" will act to separate the trocar assembly 60 from the housing 110 of the trocar coupling assembly 100. This allows removal of the trocar assembly 60 for cleaning, replacement, etc. The housing 110 includes a cover 115.

Figure 4A:
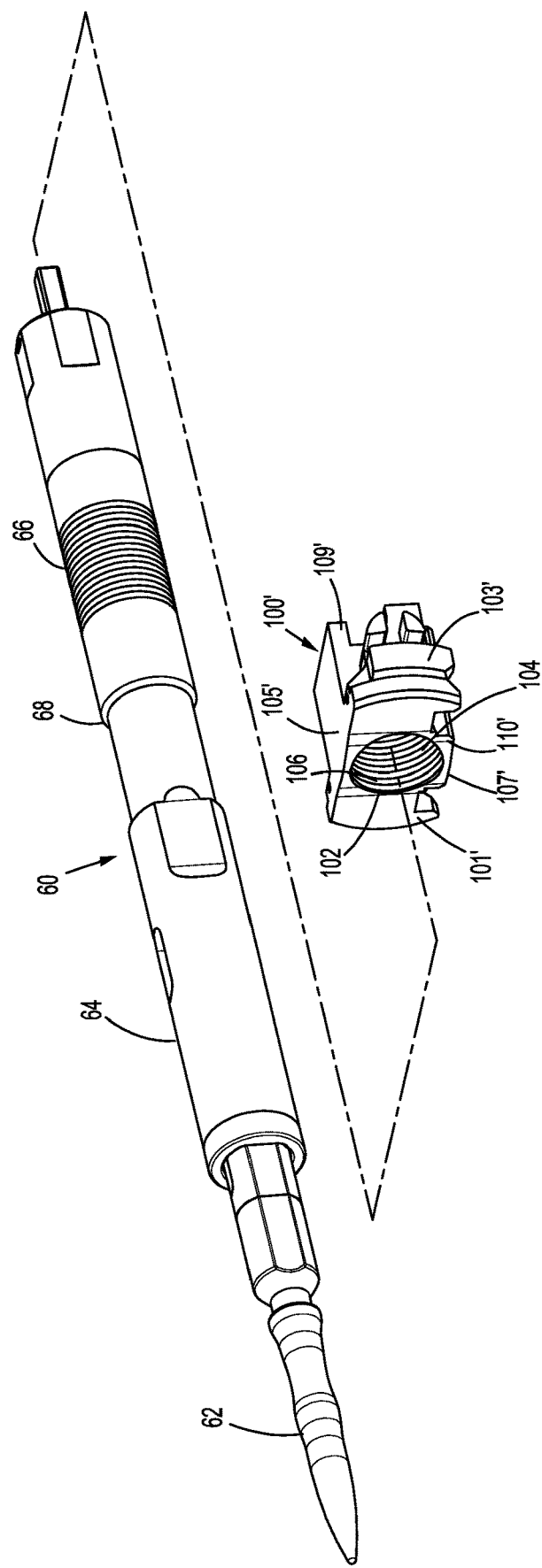
FIG. 4A is an exploded perspective view, with parts separated, of the trocar assembly and the trocar coupling assembly of FIG. 2.
Figure 12:
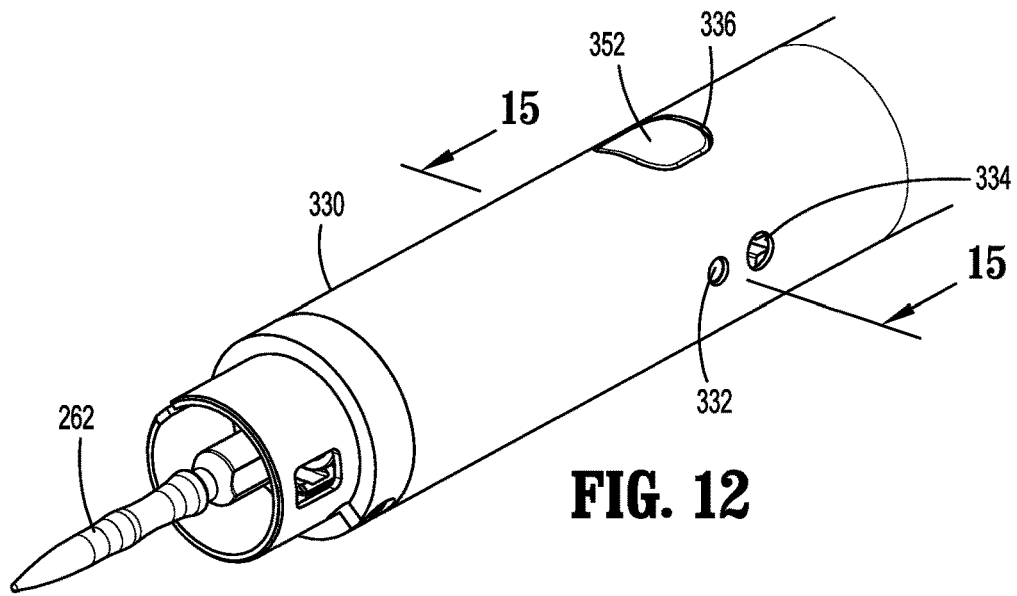
FIG. 12 is a perspective view of a distal region of a tubular shaft according to another embodiment of the present disclosure.

With additional reference to FIG. 4A, an embodiment of a trocar coupling assembly is shown and generally referenced as 100'. The trocar coupling assembly 100' has a housing 110' with a planar end face 101', arcuate side faces 103', planar top and bottom faces 105', 107', and a protrusion 109' extending from a distal portion of the housing 110'. The protrusion 109' has an open proximal end (not shown) that in conjunction with open distal end 102 defines a passage 104 therebetween. The passage 104 includes internal threads 106. The trocar assembly 60 attaches to and detaches from the trocar coupling assembly 100' similar to way the trocar assembly 60 attaches to and detaches from the load sensor 100. The trocar assembly 60 may be threadably engaged with either the load sensor 100 or the trocar coupling assembly 100'.

Another embodiment of the trocar coupling assembly is illustrated in FIGS. 5-11 and identified as trocar coupling assembly 200. With initial reference to FIGS. 5-7, a tubular shaft 230 includes an open distal end for receiving a trocar assembly 260 therein. The tubular shaft 230 may be substituted for tubular shaft 30 and coupled to the housing 20 of the surgical stapler 10. The tubular shaft 230 has openings 232 that are separated by 180° and extend through an outer wall of the tubular shaft 230. Ports 234 are also disposed on the tubular shaft, extend through the outer wall of the tubular shaft 230, and are positioned adjacent to the openings 232. The ports 234 allow for flushing of the device for cleaning the internals of the device after performing a surgical procedure. A screw 240 is located in each opening 232. As shown in FIG. 5, a tool 70 is adapted for advancing and retracting the screws 240. The tool 70 includes a body portion 72 having a proximal flange 74 with a protrusion 76 positioned on a surface thereof. A finger 78 extends from the protrusion 76 and is adapted for engaging a recess 244 of a head 242 of the screw 240 (FIG. 9). Although illustrated as having a hexagonal configuration, it is contemplated that other suitable configurations (e.g., square, star, etc.) may be used instead.

With additional reference to FIG. 8, the screws 240 are threadably coupled to the housing 210 via threaded bores 222 that are disposed in opposed cavities 220. The threaded bores 222 extend through a wall of the housing 210 such that threads 224 of the threaded bores 222 are visible in passage 204 of the housing 210. The trocar assembly 260 includes a trocar member 262 extending from a sleeve 264. The sleeve 264 includes openings 266 that are separated by 180° and extend through an outer surface of the sleeve 264. Each opening is configured to receive a portion of a shaft 246 (FIG. 11) of the screw 240. In particular, the housing 210 is positioned in a lumen of the tubular shaft 230 such that the heads 242 of the screws 240 are aligned with the openings 232 in the tubular shaft 230. As such, the finger 78 of the tool 70 is insertable into each of the recesses 244 since they are accessible through the openings 232. This arrangement allows the clinician to tighten or loosen the screws 240 using the tool 70. Initially, the screws 240 are in a retracted configuration (FIG. 11) allowing the trocar assembly 260 to be inserted into and/or removed from the trocar coupling assembly 200. Once the trocar assembly 260 is fully seated in the housing 210 of the trocar coupling assembly 200, the clinician inserts a tip of the finger 78 into the recess 244 of the head 242 of the screw 240 and rotates the tool 70 to tighten (i.e., advance) the screw 240 such that a portion of the shaft 246 extends into the opening 266 in the sleeve 264 of the trocar assembly 260 (FIGS. 8-10) and defines a locked configuration of the trocar coupling assembly 200. It is contemplated that tightening one of the screws 240 is sufficient to lock the trocar assembly 260 in the trocar coupling assembly 200. This arrangement securely couples the trocar assembly 260 to the tubular shaft 230 via the trocar coupling assembly 200. Conversely, with the tip of the finger 78 inserted in the recess 244 of the head 242 of the screw 240, the tool 70 is rotated in the opposite direction to loosen (i.e., retract) the screw 240 and withdraw the portion of the shaft 246 from the opening 266 in the sleeve 264 of the trocar assembly 260. The head 242 of the screw 240 has an outer diameter that is greater than a diameter of the opening 232, which acts as a stop to limit the travel distance of the screw 240 as it is being loosened. Once the screw 240 is fully loosened (FIG. 11), the trocar assembly 260 may be removed from the lumen of the tubular shaft 230. This is the unlocked configuration of the trocar coupling assembly 200, which allows insertion and/or removal of the trocar assembly 260.

Referring now to FIGS. 12-17, a further embodiment of the trocar coupling assembly is illustrated and identified as trocar coupling assembly 300. The trocar coupling assembly 300 is positionable within a lumen of a tubular shaft 330. The tubular shaft 330 may be substituted for tubular shaft 30 or tubular shaft 230 and coupled to the housing 20 of the surgical stapler 10. The tubular shaft 330 has a lumen extending therethrough with an open distal end. The tubular shaft 330 has openings 332 that are separated by 180° and extend through an outer wall of the tubular shaft 330. Ports 334 are also disposed on the tubular shaft, extend through the outer wall of the tubular shaft 330, and are positioned adjacent to the openings 332. The ports 334 allow for flushing of the device for cleaning the internals of the device after performing a surgical procedure. A buttonhole 336 is situated on an outer surface of the tubular shaft 330 between the openings 332 (FIG. 12) and allows access to a release button 350. The trocar assembly 260 (FIG. 7) is insertable into and removable from the lumen of the tubular shaft 330 through the open distal end. The trocar coupling assembly 300 includes a housing 310, a clip 320, and retention pins 340. Operation of the release button 350, as will be described in further detail below, transitions the trocar coupling assembly 300 between the locked (FIG. 15) and unlocked (FIG. 17) configurations.

Figure 13:
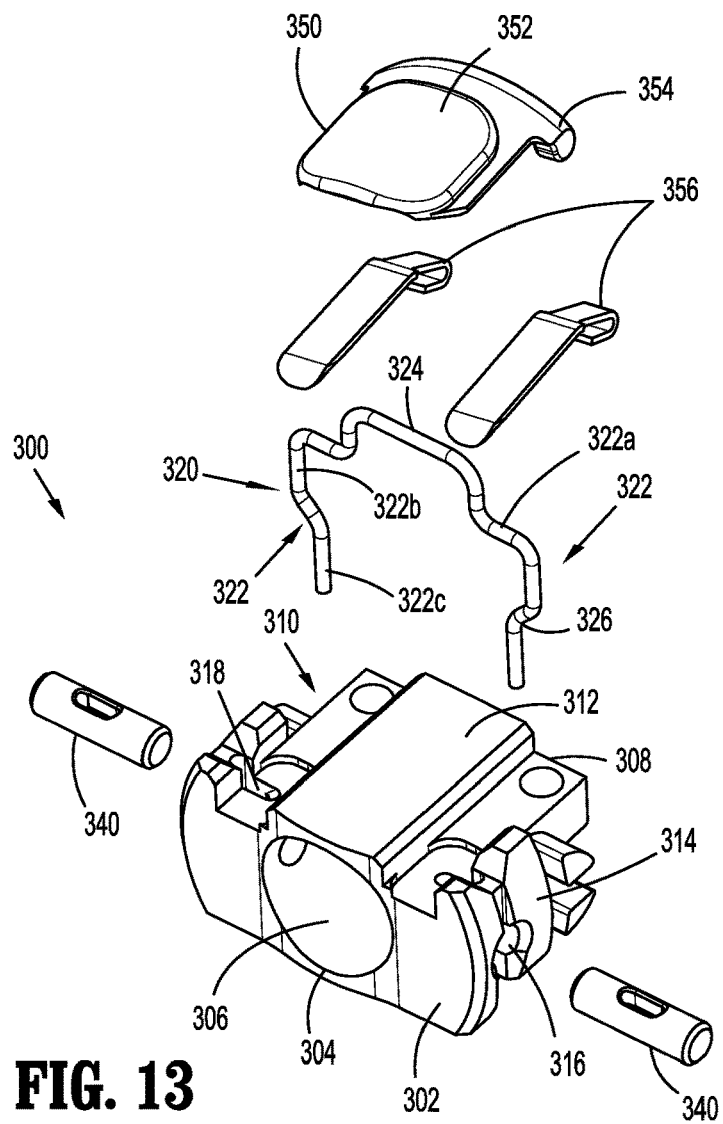
FIG. 13 is an exploded perspective view, with parts separated, of the trocar coupling assembly of FIG. 12.
Figure 14:
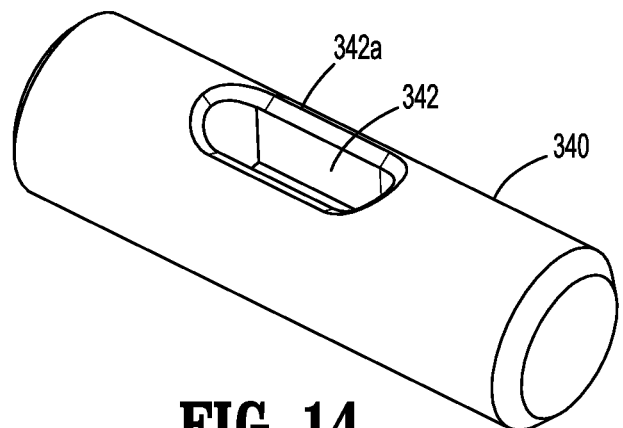
FIG. 14 is a perspective view of a retention pin of the trocar coupling assembly of FIG. 13.
Figure 15:
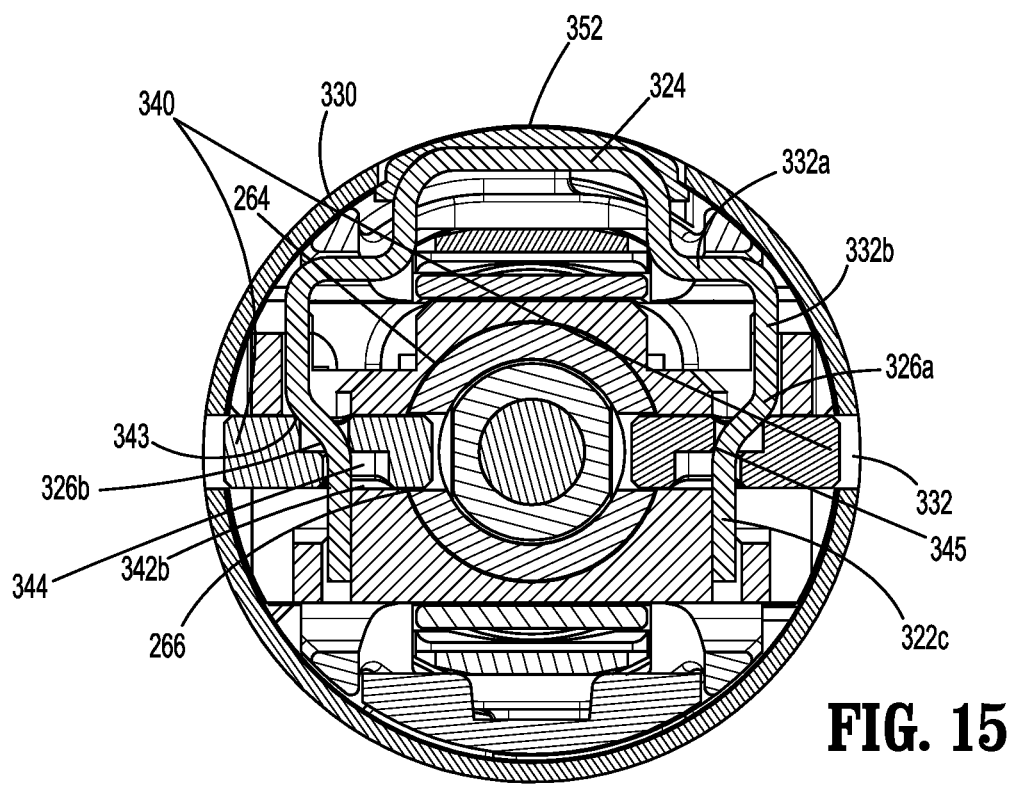
FIG. 15 is an end cross-sectional view of the distal region of the tubular shaft of FIG. 12 taken along section line 15-15 of FIG. 12 depicting a locked configuration of the trocar coupling assembly.
Figure 17:
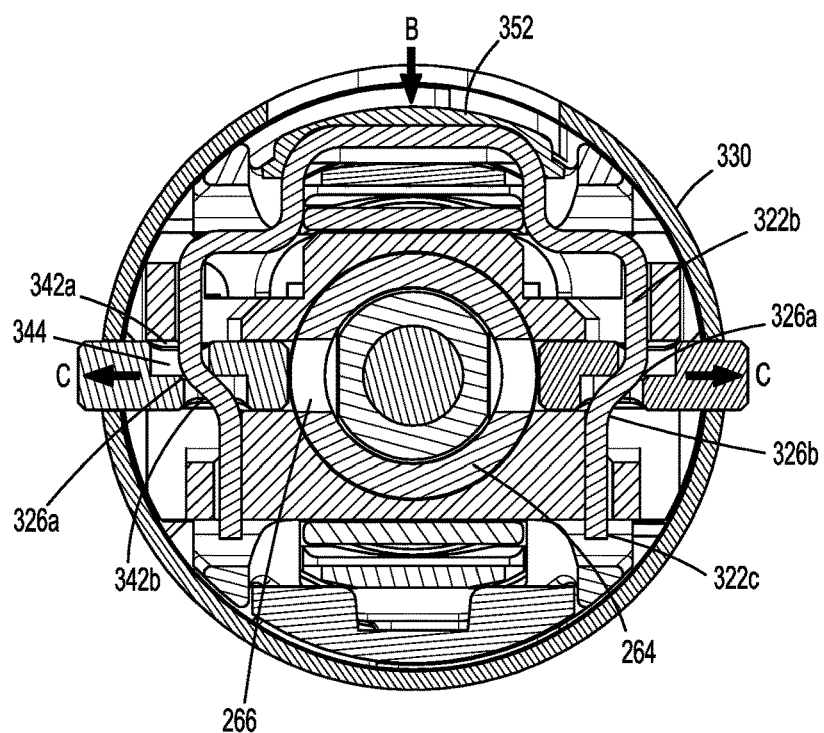
FIG. 17 is an end cross-sectional view of the distal region of the tubular shaft of FIG. 16 taken along section line 17-17 of FIG. 16 depicting an unlocked configuration of the trocar coupling assembly.

As seen in FIG. 13, the housing 310 of the trocar coupling assembly 300 has a planar distal face 302 with an opening 304. A passage 306 extends from the opening 304 to an opening (not shown) on a proximal face 308 of the housing 310. A top surface 312 of the housing 310 has a planar configuration for supporting leaf springs 356. Leaf springs 356 bias the release button 350 away from the top surface 312. The housing 310 has side surfaces 314. Each side surface 314 includes a chamber 316 that is configured for slidably receiving the retention pin 340. A bore 318 extends transverse to the chamber 316 and intersects it. The bore 318 is configured for slidably receiving a leg 322 of the clip 320. The clip 320 is generally U-shaped and includes a backspan 324. Each leg 322 has a first section 322a, a second section 322b, and a third section 322c. The first section 322a is parallel to the backspan 324 while the second and third sections 322b, 322c are perpendicular to the backspan 324. Further, the second and third sections, 322b, and 322c, are laterally spaced apart while remaining substantially parallel to one another and the first section 322a is perpendicular to the second and third sections 322b, 322c. As shown in FIGS. 13 and 14, the retention pin 340 is generally cylindrical with a slot 342 that has opposed openings 342a, 342b. The openings 342a, 342b are 180° apart and longitudinally spaced apart (FIG. 15). As seen in FIGS. 15 and 17, the staggered arrangement of the openings 342a, 342b defines an ess shaped pathway 344. In particular, the third section 322c of the leg 322 is inserted through the openings 342a, 342b such that a majority of the third section 322c extends through the retention pin 340. An arcuate region 326 joins the second and third sections 322b, 322c of the leg 322 and a linear portion 328 connects the first and second sections 322a, 322b. In the locked configuration (FIG. 15), with the majority of the third section 322c inserted through the opening 342b, the arcuate region 326 is partially inserted into the pathway 344 such that a first portion 326a of the arcuate region 326 contacts an outboard edge 343 of the slot 342. The curved profile of the arcuate region 326 allows the third section 322c to exit the opposing opening 342b while a second portion 326b of the arcuate region 326 contacts an inboard edge 345 of the slot 342. This arrangement biases the retention pin 340 towards a center of the tubular shaft 330 (i.e., inboard). Shoulders that are located in the lumen of the tubular shaft 330 engage the first sections 322a of the legs 322 and act as a limit stop for the clip 320. The backspan 324 of the clip 320 engages the underside of the release button 350. A portion of each retention pin 340 extends through the opening 266 in the trocar assembly 260 and locks the trocar assembly 260 in position.

Figure 16:
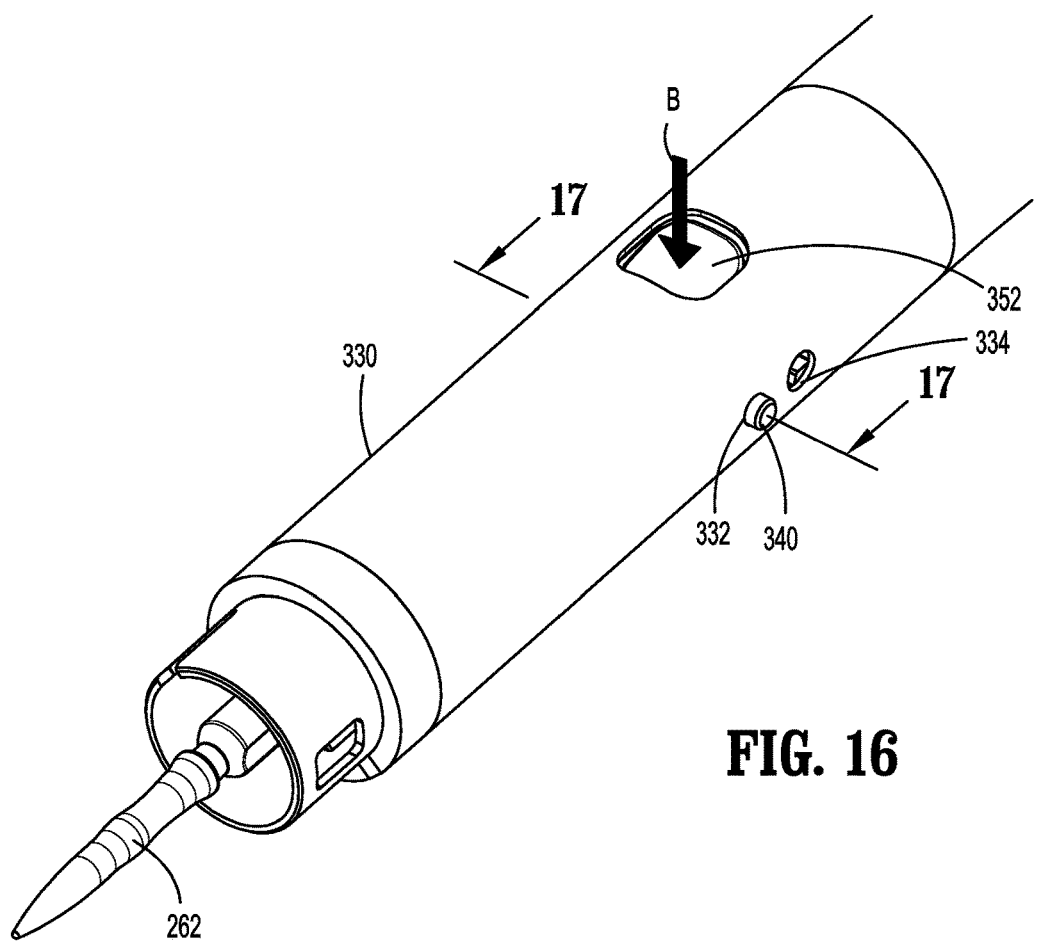
FIG. 16 is a perspective view of the distal region of the tubular shaft of FIG. 12 showing the release button in a compressed configuration and the retention pin extended.

With additional reference to FIGS. 16 and 17, depressing the release button 350 overcomes the bias of leaf springs 356 and moves the release button 350 towards the lumen of the tubular shaft 330. As the underside of the release button 350 and the backspan 324 of the clip 320 are in contact with one another, movement of the release button 350 towards the lumen of tubular shaft 330 also moves the clip 320 in the same direction as indicated by arrow "B". The second sections 322b of the clip 320 slide through the bores 318 along with the first portions 326a of the arcuate regions 326, which cams against the outboard edges 343 of the slots 342. This urges the retention pins 340 away from the lumen of the tubular shaft 330 (i.e., outboard) in the direction of arrow "C". Simultaneously, portions of the retention pins 340 are withdrawn from the openings 266 in the trocar assembly 260 allowing the trocar assembly 260 to be removed from the trocar coupling assembly 300. In this unlocked configuration of the trocar coupling assembly 300, the trocar assembly 260 may be inserted into the tubular shaft 330.

The release button 350 has an outer surface 352 that extends through the buttonhole 336 of the tubular shaft 330 (FIG. 12) and is flush with an outer surface of the tubular shaft 330. The release button 350 also includes a skirt 354 attached to an underside of the release button 350. As the skirt 354 is larger than the buttonhole 336, contact between the skirt 354 and an inner surface of the lumen of the tubular shaft 330 limits the travel of the release button 350 due to a perimeter of the skirt 354 contacting an inner surface of the tubular shaft 330 that prevents further upward travel of the release button 350. With the release button 350 fully extended under the bias of the leaf springs 356 (FIG. 15), the trocar coupling assembly 300 is in the locked configuration and retains the trocar assembly 260 in the lumen of the tubular shaft 330 or prevents insertion of the trocar assembly 260 into the trocar coupling assembly 300. By depressing the release button 350 and overcoming the bias of the leaf springs 356 (FIG. 17), the trocar coupling assembly 300 is transitioned to the unlocked configuration allowing the trocar assembly 260 to be inserted or removed from the tubular shaft 330.

Figure 18:
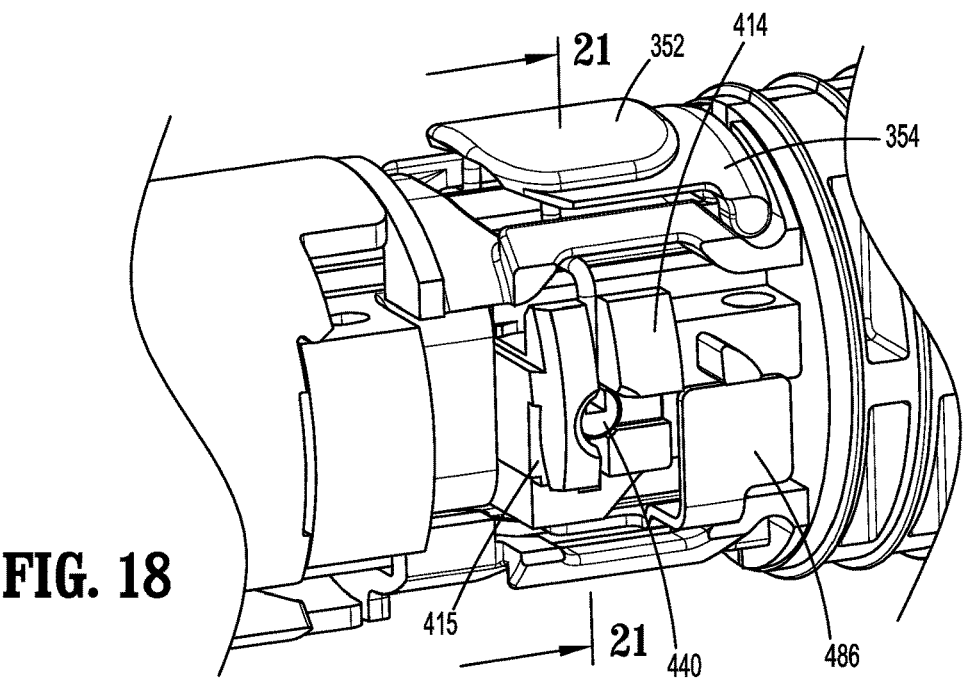
FIG. 18 is a perspective view of a portion of a tubular shaft with an outer tube removed illustrating a trocar coupling assembly according to an embodiment of the present disclosure.
Figure 19:
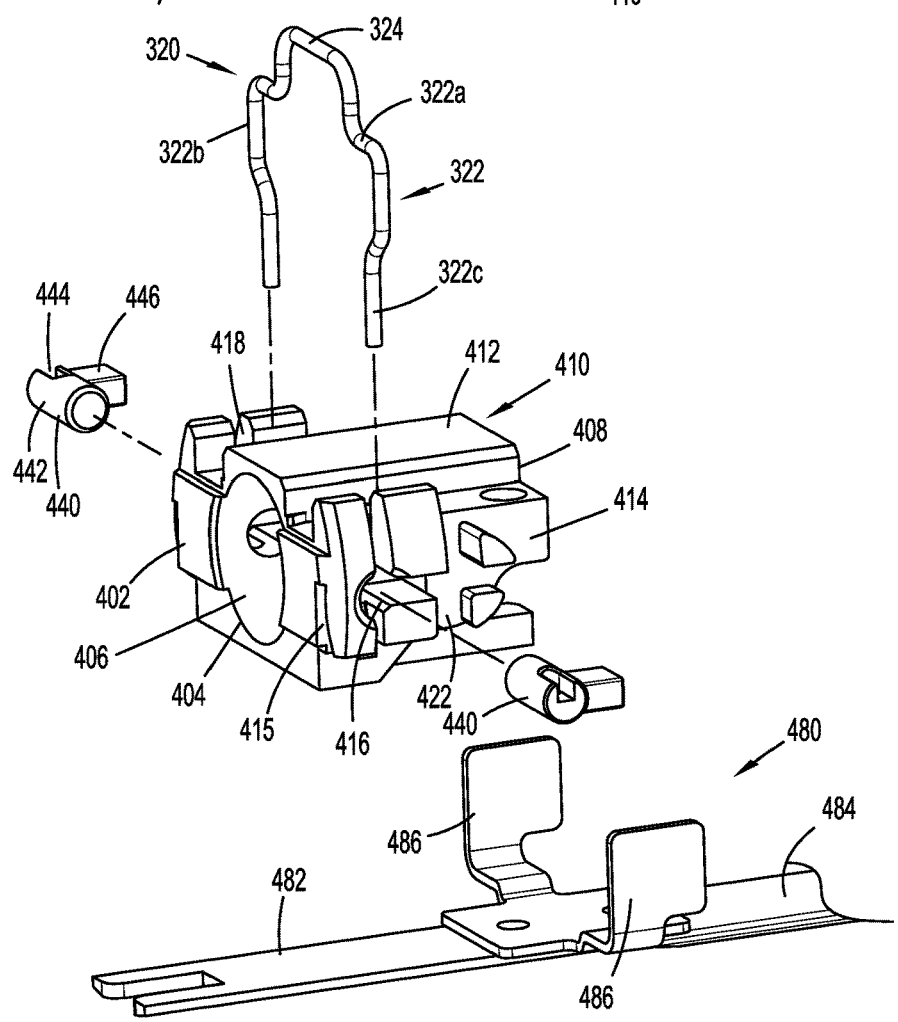
FIG. 19 is an exploded perspective view, with parts separated, of the trocar coupling assembly of FIG. 18.
Figure 20:
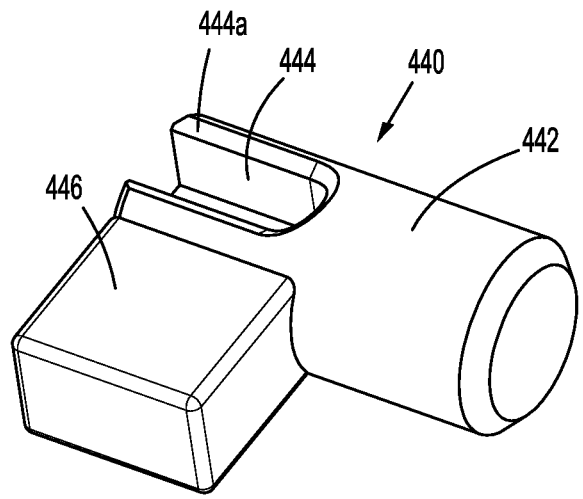
FIG. 20 is a perspective view of a retention pin of the trocar coupling assembly of FIG. 19.
Figure 24:
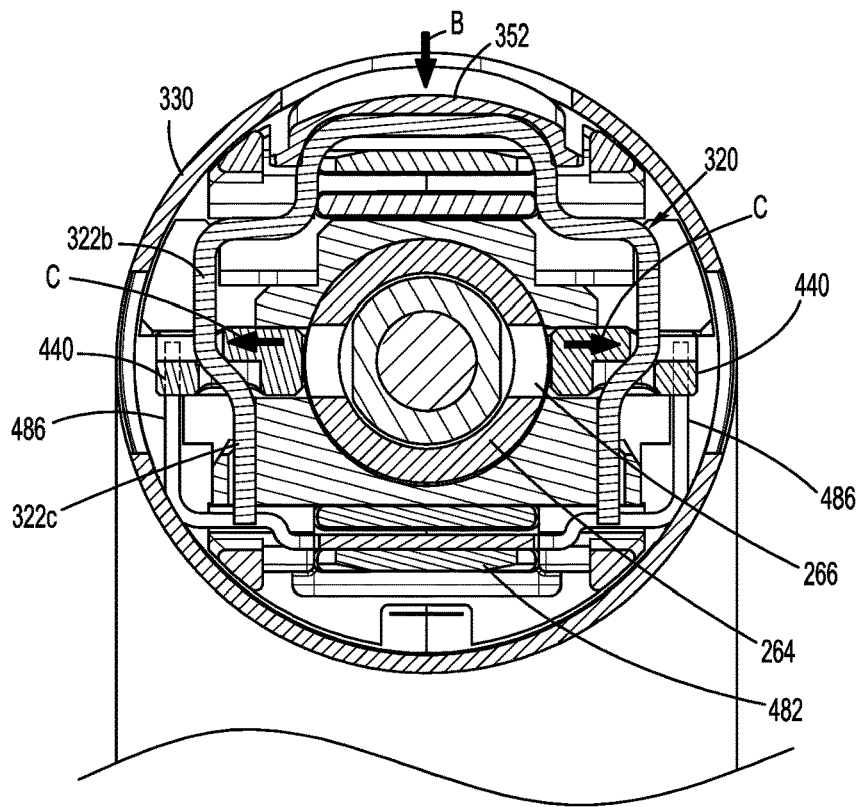
FIG. 24 is an end cross-sectional view of the tubular shaft and trocar coupling assembly of FIG. 18 depicting the trocar coupling assembly in an unlocked configuration.

Another embodiment of the trocar coupling assembly is illustrated in FIGS. 18-20 and identified as trocar coupling assembly 400. The trocar coupling assembly 400 is positionable within the lumen of the tubular shaft 330 and includes a housing 410 and the clip 320 of trocar coupling assembly 300. The trocar coupling assembly 400 also includes retention pins 440 and an interlock 480. The interlock 480 is operatively coupled to an actuation mechanism of surgical stapler 10 and translates proximally and distally through the tubular shaft 330 during actuation of the surgical stapler 10. Each retention pin 440 includes a cylindrical body portion 442 having a slot 444 disposed at one end of the body portion 442. A rectangular tab 446 extends from the body portion 442 in the proximity of the slot 444. The housing 410 includes a planar distal face 402 with an opening 404. A passage 406 extends from the opening 404 to an opening (not shown) on a proximal face 408 of the housing 410. A top surface 412 of the housing 410 has a planar configuration for supporting leaf springs 356 (see FIG. 13). The leaf springs 356 bias the release button 350 away from the top surface 412. The housing 410 has side surfaces 414. Each side surface 414 includes a chamber 416 that is configured for slidably receiving a retention pin 440. A bore 418 extends transverse to the chamber 416 and intersects it. The bore 418 is configured for slidably receiving the leg 322 of the clip 320. A slot 422 extends from the chamber 416 and is configured to slidably receive the tab 446 of the retention pin 440 therein, which allows the retention pin 440 to slide between an inserted configuration (FIG. 21) and a withdrawn configuration (FIG. 24). The placement of the tab 446 in slot 422 also maintains the alignment of the retention pin 440 relative to the housing 410. A cutout 415 extends along the longitudinal axis of the passage 406 and intersects the chamber 416 and the slot 422. With additional reference to FIG. 21, a distal portion of the third section 322c of leg 322 is disposed in the slot 442. Similar to the retention pin 340, the slot 444 has opposed openings 444a, 444b that are separated by 180° and define an ess shaped pathway 448. The third section 322c of the leg 322 is inserted through the openings 444a, 444b such that the majority of the third section 322c extends through the retention pin 440. With the majority of the third section 322c inserted through the opening 442b, the arcuate region 326 is partially inserted into the pathway 448 such that a first portion 326a of the arcuate region 326 contacts an outboard edge 443 of the slot 442. The curved profile of the arcuate region 326 allows the third section 322c to exit the opposing opening 442b while the second portion 326b of the arcuate region 326 contacts an inboard edge 445 of the slot 442. This arrangement biases the retention pin 440 towards a center of the tubular shaft 330 (i.e., inboard). Shoulders that are located in the lumen of the tubular shaft 330 engage the first sections 322a of the legs 322 and act as a limit stop for the clip 320. The backspan 324 of the clip 320 engages the underside of the release button 350. A portion of each retention pin 440 extends through the opening 266 in the trocar assembly 260 and locks the trocar assembly in position.

Figure 21:
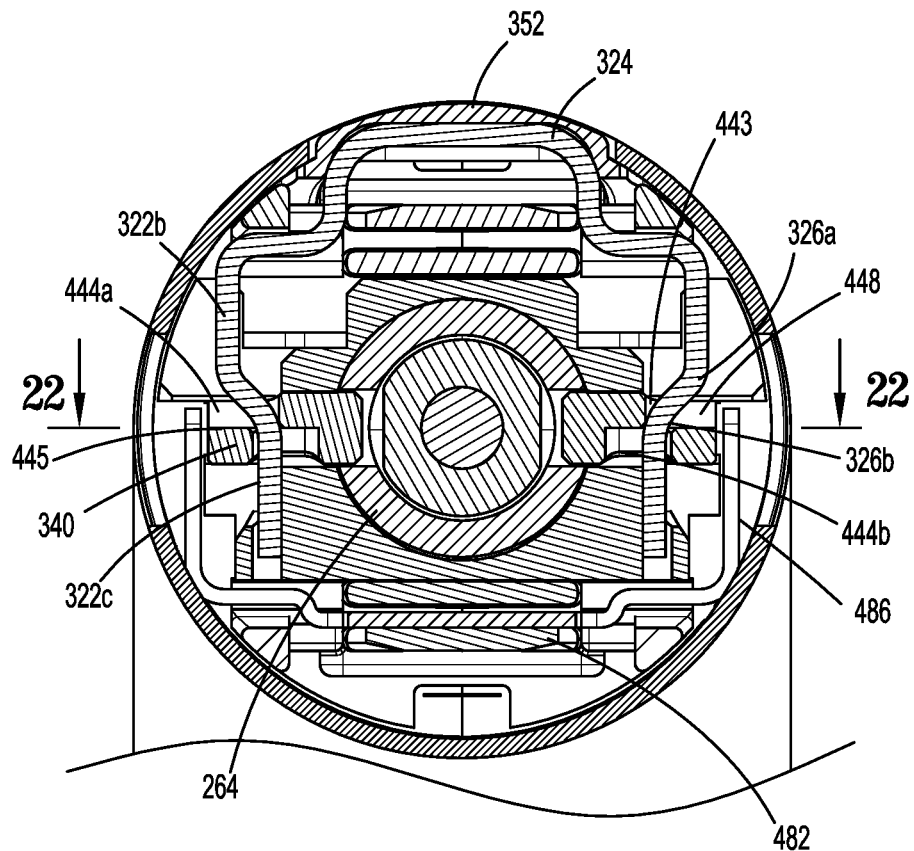
FIG. 21 is an end cross-sectional view of the tubular shaft of FIG. 18 taken along section line 21-21 of FIG. 18 depicting the trocar coupling assembly in a locked configuration.

With continued reference to FIG. 21 and further reference to FIG. 24, actuation of the trocar coupling assembly 400 is illustrated. Similar to the actuation of the trocar coupling assembly 300 (FIGS. 15 and 17), transitioning the trocar coupling assembly 400 between the locked (FIG. 21) and unlocked configurations (FIG. 24) involves actuating the release button 350. Depressing the release button 350 overcomes the bias of the leaf springs 356 (FIG. 13) and moves the release button 350 towards the lumen of the tubular shaft 330. As the underside of the release button 350 is in contact with the backspan 324 of the clip 320, the movement of the release button 350 towards the lumen of the tubular shaft 330 also moves the clip 320 in the same direction as indicated by arrow "B" (FIG. 24). The second sections 322b of the legs 322 slide through the bores 418 along with the first portions 326a of the arcuate regions 326 that cam against the outboard edges 443 of the slots 442. This urges the retention pins 440 away from the lumen of the tubular shaft 330 (i.e., outboard) in the direction of arrow "C" (FIG. 24). Simultaneously, portions of the retention pins 440 are withdrawn from the openings 266 in the trocar assembly 260 allowing the trocar assembly 260 to be removed from the trocar coupling assembly 400. In this unlocked configuration of the trocar coupling assembly 400, the trocar assembly 260 may be inserted into the tubular shaft 330 and into the trocar coupling assembly 400. Conversely, releasing the release button 350 allows the bias of the leaf springs 356 to urge the release button towards the fully extended position and defining the locked configuration of the trocar release assembly 400.

Figure 22:
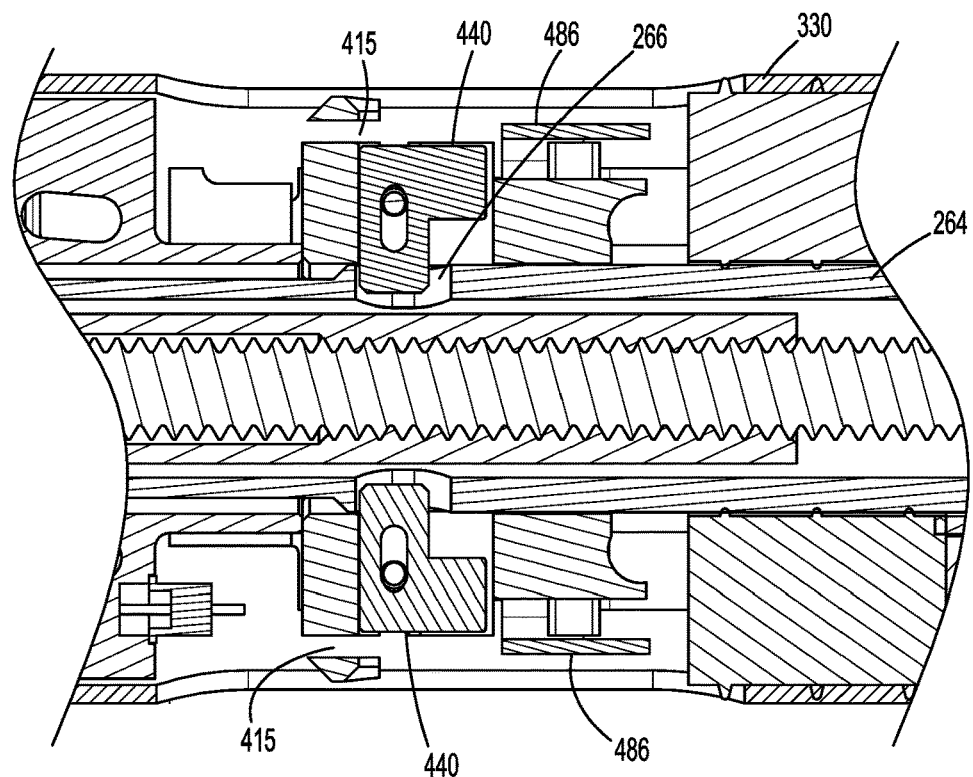
FIG. 22 is a top cross-sectional view of the tubular shaft and trocar coupling assembly of FIG. 18 taken along section line 22-22 of FIG. 21 showing a plate in a retracted position.
Figure 23:
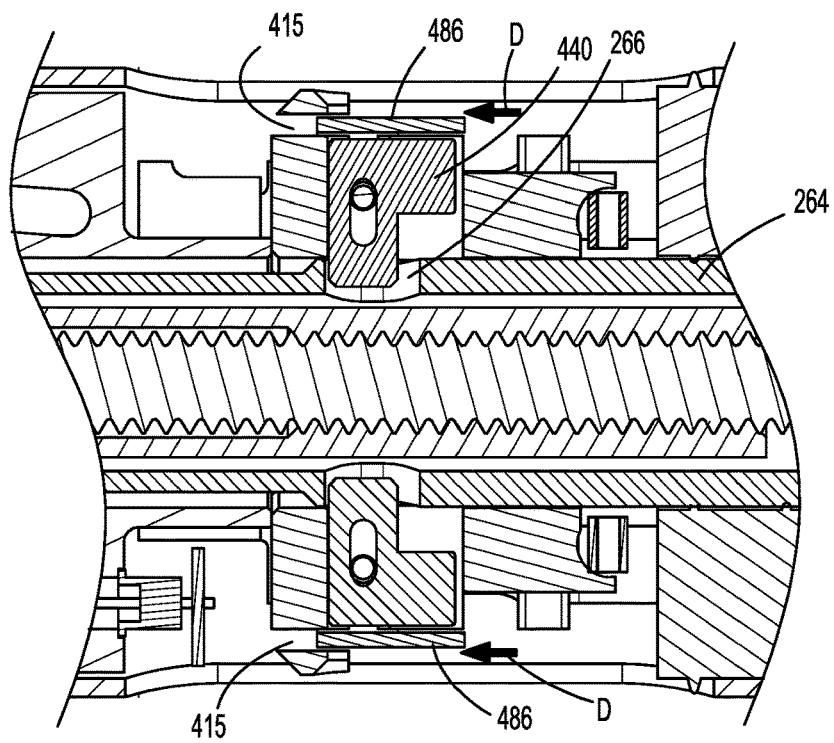
FIG. 23 is a top cross-sectional view of the tubular shaft and trocar coupling assembly of FIG. 22 showing the plate in an extended position.
Figure 25:
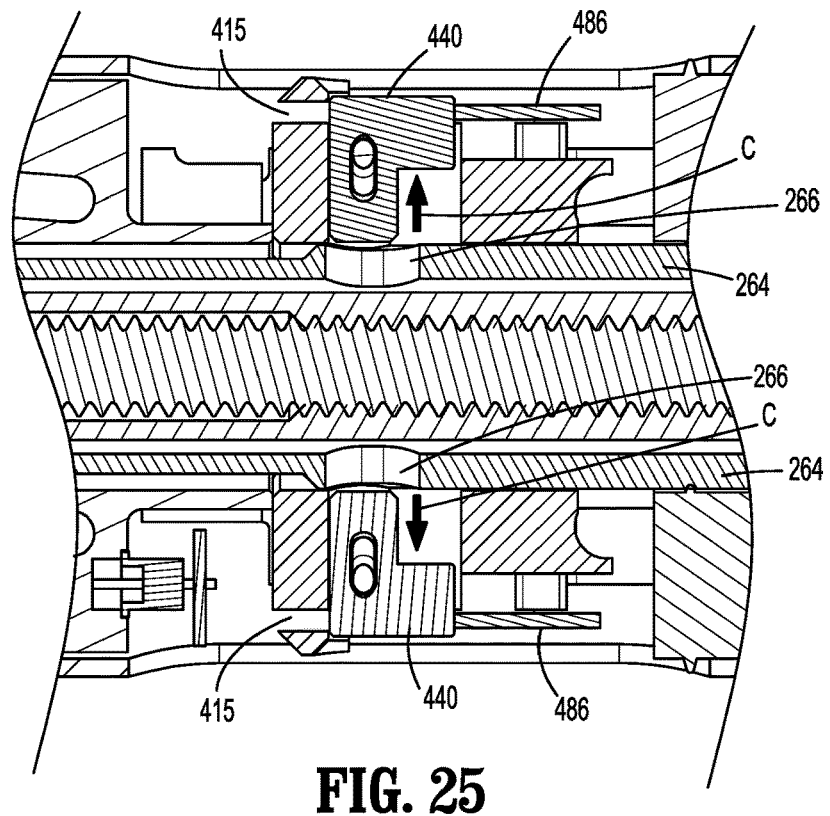
FIG. 25 is a top cross-sectional view of the tubular shaft and trocar coupling assembly of FIG. 22 depicting the trocar coupling assembly in an unlocked configuration.
Figure 26:
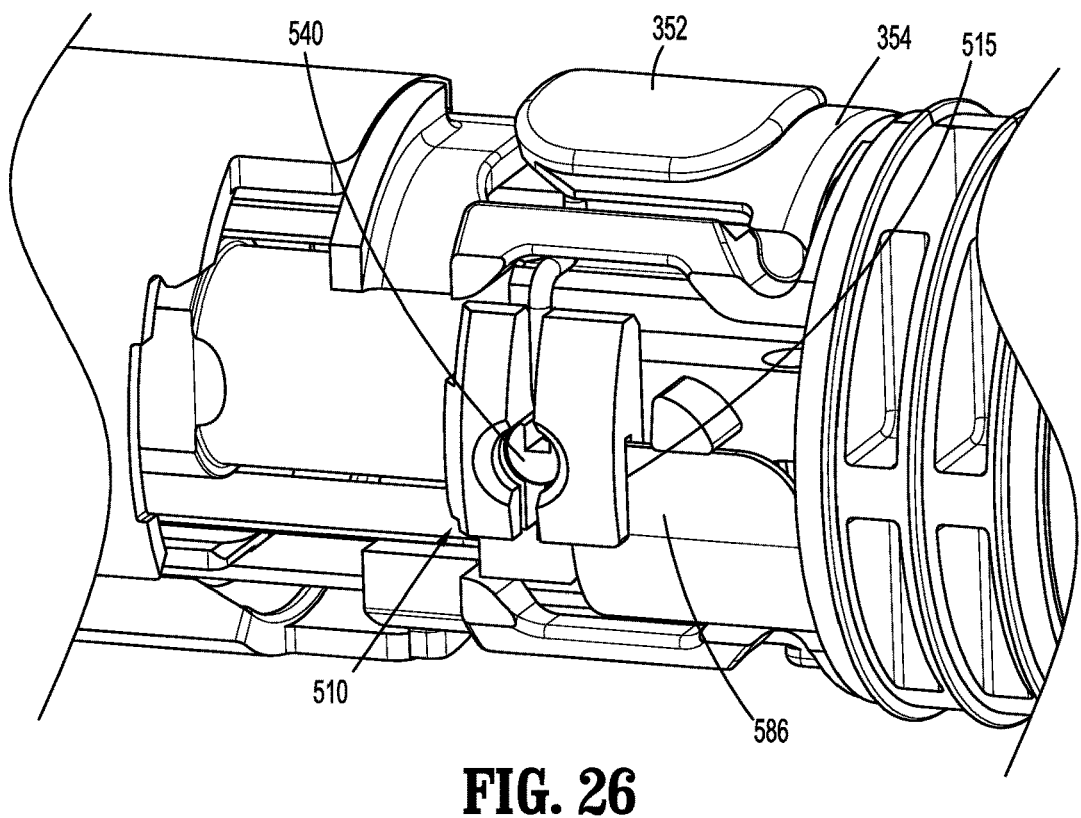
FIG. 26 is a perspective view of a tubular shaft with an outer tube removed and a trocar coupling assembly according to a further embodiment of the present disclosure.
Figure 27:
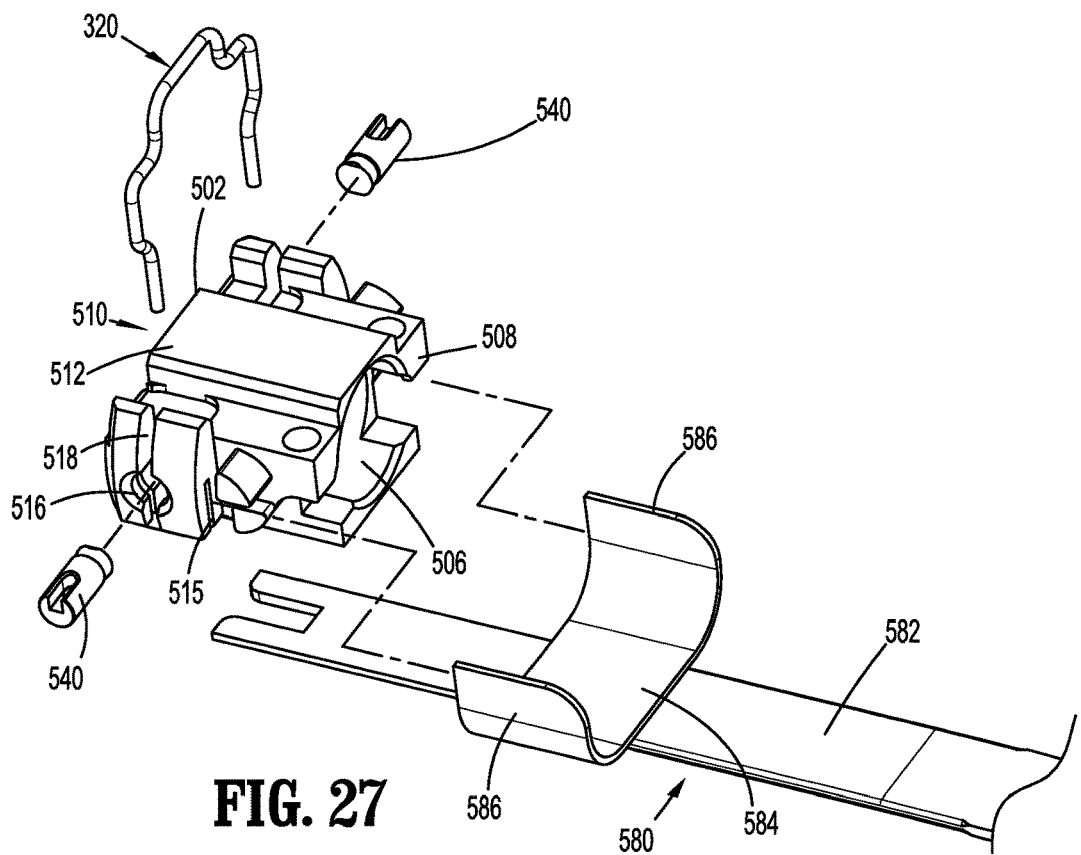
FIG. 27 is an exploded perspective view, with parts separated, of the trocar coupling assembly of FIG. 26.

With additional reference to FIGS. 22, 23, and 25, the trocar coupling assembly 400 also includes the interlock 480. As seen in FIG. 19, the interlock 480 has an elongate drive band 482 with a shield 484 welded to the drive band 482. The shield 484 includes plates 486 extending in a direction that is orthogonal to the drive band 482. The plates 486 are parallel to one another and spaced apart by a distance that is greater than a width of the drive band 482 and wide enough for the plates 486 to slide within the lumen of the tubular shaft 330 without contacting an inner surface of the tubular shaft 330 and slide through the cutouts 415 of the housing 410 in the direction of arrow "D" (FIG. 23). With the trocar assembly 260 inserted into the trocar coupling assembly 400 and the trocar coupling assembly 400 in the locked configuration (FIG. 22), the plates 486 are uninhibited and are movable proximally and distally during movement of the interlock 480 as part of the operation of the surgical stapler 10 (FIG. 23). When the trocar coupling assembly 400 is in the unlocked configuration (FIG. 24), the retention pins 440 are moved in the direction of arrow "C" (i.e., outboard) and are withdrawn from the openings 266 of the trocar assembly 260. When the retention pins 440 are moved outboard, the tabs 446 are positioned in the cutouts 415 and block movement of the plates 486 and the interlock 480. This arrangement inhibits actuation of the surgical stapler 10 when the trocar coupling assembly 400 is in the unlocked configuration. Thus, during insertion or removal of the trocar assembly 260 from the surgical stapler 10, the extension of the retention pins 440 to block movement of the plates 486 prevents actuation of the drive mechanism of the surgical stapler 10. Additionally, this arrangement also prevents actuation of the drive mechanism of the surgical stapler 10 in the absence of a trocar assembly being coupled with the trocar coupling assembly 400.

Figure 28:
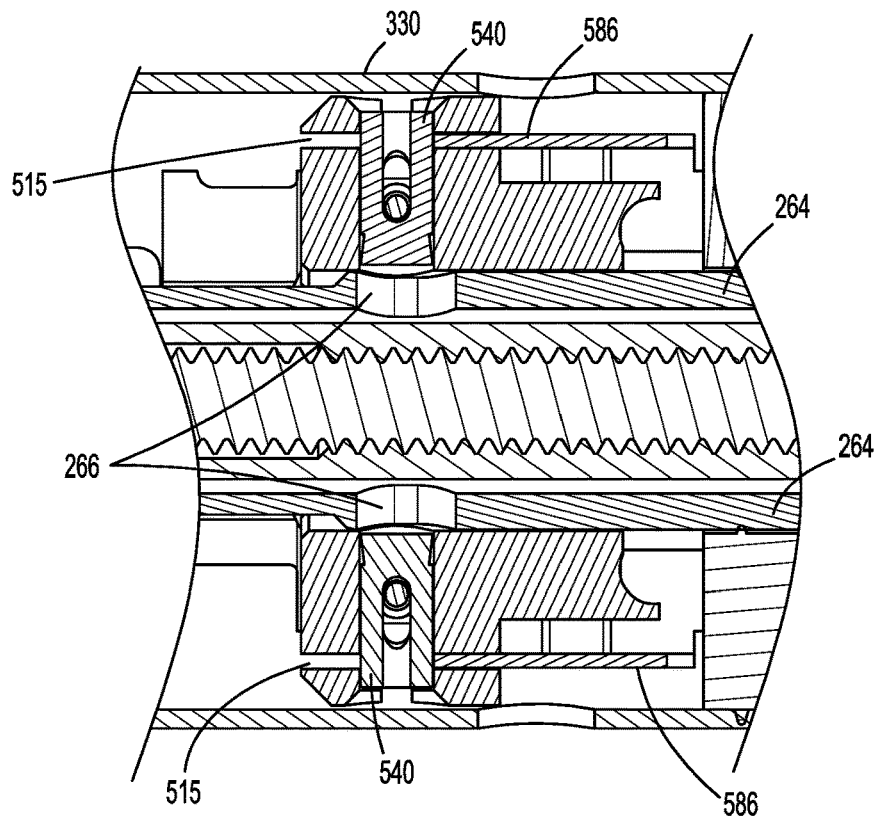
FIG. 28 is a top cross-sectional view of the tubular shaft and trocar coupling assembly of FIG. 26 with the trocar coupling assembly in an unlocked configuration.
Figure 29:
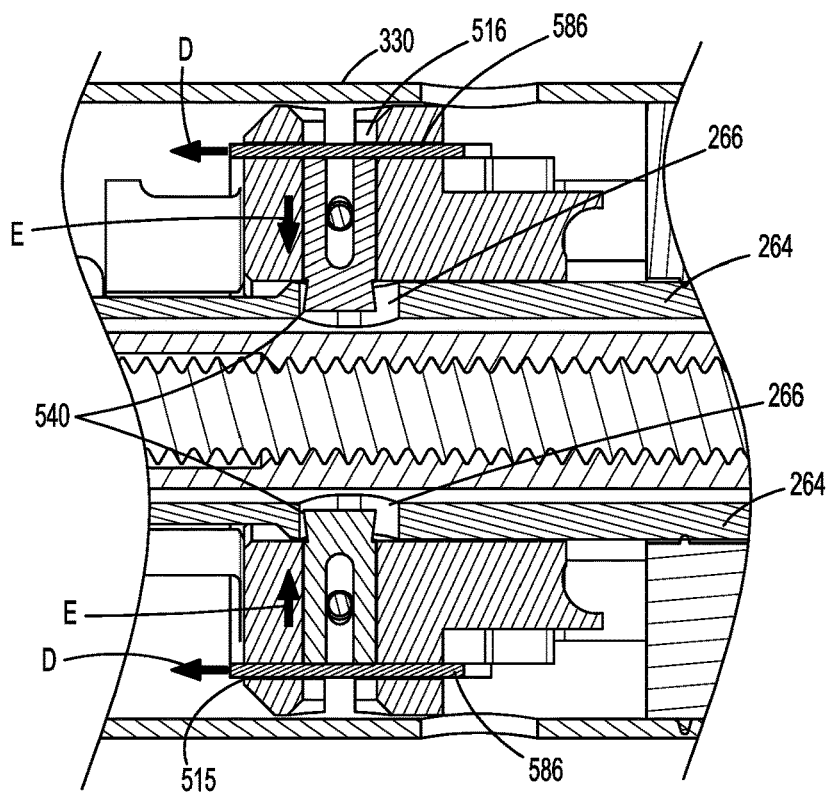
FIG. 29 is a top cross-sectional view of the tubular shaft and trocar coupling assembly of FIG. 26 with the trocar coupling assembly in a locked configuration.

Referring now to FIGS. 26-29, a further embodiment of the trocar coupling assembly is shown and identified as trocar coupling assembly 500. Trocar coupling assembly 500 includes a trocar housing 510, retention pins 540, and the clip 320 that was previously described with reference to the trocar coupling assemblies 300, 400. The housing 510 has a distal surface 502, a proximal surface 508, and a passage 506 extending therebetween. A top surface 512 of the housing 510 is planar for supporting leaf springs 356 (FIG. 13). Side surfaces 514 of the housing 510 include chambers 516 for slidably receiving retention pins 540 and bores 518 that intersect the chambers 516 and allow legs 322 of the clip 320 to slide therein. Additionally, the side surfaces 514 include cutouts 515 that extend along a longitudinal axis of the housing 510. The retention pins 540 are similar to the retention pins 440, but lack the tabs 446 while retaining the remaining structures of the retention pins 440. In this embodiment, the trocar coupling assembly 500 includes an interlock 580 that is movable in the direction of arrow "D" (FIG. 29). The interlock 580 includes a drive band 582 with a U-shaped cradle 584 welded to the drive band 582. The guard 584 includes opposed plates 586 that extend in a direction that is orthogonal to the drive band 582. Similar to the plates 486 of trocar coupling assembly 400, the plates 586 of trocar coupling assembly 500 are parallel to one another and spaced apart by a distance that is greater than a width of the drive band 582 and wide enough for the plates 586 to slide within the lumen of the tubular shaft 330 without contacting an inner surface of the tubular shaft 330 and slide through the cutouts 515 of the housing 510. The operation of the trocar coupling assembly 500 is substantially similar to that of the trocar coupling assembly 400 and this is shown in FIGS. 28 and 29. In the unlocked configuration of the trocar coupling assembly 500 (FIG. 28), the retention pins 540 are withdrawn from the openings 266 of the trocar assembly 260 and block the path of the plates 586 such that the plates 586 and the drive band 582 are blocked from moving past the housing 510. Thus, during insertion or removal of the trocar assembly 260 from the surgical stapler 10, the extension of the retention pins 540 to block movement of the plates 586 prevents actuation of the drive mechanism of the surgical stapler 10. Additionally, this arrangement also prevents actuation of the drive mechanism of the surgical stapler 10 in the absence of a trocar assembly being coupled with the trocar coupling assembly 500. Conversely, with the trocar coupling assembly 500 in the locked configuration (FIG. 29), the retention pins 540 move in the direction of arrow "E" and are inserted into the openings 266 of the trocar assembly 260 and are out of the path of the plates 586 as they slide proximally and distally through the cutouts 515.

It will be understood that various modifications may be made to the embodiments disclosed herein. Therefore, the above description should not be construed as limiting, but merely as exemplifications of particular embodiments. Those skilled in the art will envision other modifications within the scope and spirit of the claims appended hereto.

What is claimed is:

1. A trocar coupling assembly for a surgical stapler comprising:
    a housing having opposed openings defining a passage therethrough, the passage configured to receive a sleeve of a trocar assembly therein;
    a release button movably coupled to the housing, the release button movable between a relaxed position and a compressed position;
    a spring disposed between the housing and the release button, the spring biasing the release button towards the extended position;
    a retention pin disposed in a bore of the housing and slidable between extended and retracted positions;
    a cutout located in the housing, the cutout extending parallel to the passage of the housing and intersecting the bore of the housing, the cutout configured to receive a portion of a plate; and
    a clip operatively coupling the release button and the retention pin, the clip translatable between first and second positions, the first position biasing the retention pin towards the extended position and the second position moving the retention pin to the retracted position.

2. The trocar coupling assembly of claim 1, wherein the compressed position of the release button and the retracted position of the retention pin define an unlocked configuration of the trocar coupling assembly.

3. The trocar coupling assembly of claim 2, wherein a sleeve of a trocar assembly is insertable into the passage of the housing with the trocar coupling assembly in the unlocked configuration.

4. The trocar coupling assembly of claim 2, wherein the housing is positionable in a lumen of a tubular shaft and a portion of the retention pin extends through an orifice of the tubular shaft thereby providing a visual indication that the trocar coupling assembly is in the unlocked configuration.

5. The trocar coupling assembly of claim 1, wherein the relaxed position of the release button and the extended position of the retention pin define a locked configuration of the trocar coupling assembly.

6. The trocar coupling assembly of claim 5, wherein a distal portion of the retention pin is engageable with a slot in an outer surface of a sleeve of a trocar assembly to maintain a fixed axial relationship between the trocar coupling assembly and a trocar assembly.

7. The trocar coupling assembly of claim 5, wherein the locked configuration of the trocar coupling assembly inhibits insertion of a trocar assembly into the passage of the housing.

8. The trocar coupling assembly of claim 1, wherein a leg of the clip extends through a pathway of the retention pin.

9. The trocar coupling assembly of claim 1, wherein a bottom surface of the release button engages a backspan of the clip.

10. The trocar coupling assembly of claim 1, wherein a backspan of the clip contacts a portion of the spring such that moving the release button towards the compressed position urges the spring and the clip towards a bottom surface of the housing.

11. The trocar coupling assembly of claim 1, wherein the trocar coupling assembly is positionable within a lumen of a tubular shaft.

12. The trocar coupling assembly of claim 1, wherein the plate is secured to a drive band and inhibited from movement in a distal direction with the trocar release assembly in the unlocked configuration.

13. The trocar coupling assembly of claim 12, wherein an extended position of the retention pin allows proximal and distal movement of the drive band.

14. A shaft for use with a surgical stapler, the shaft comprising:
    a tubular member;
    a trocar coupling assembly positionable in the tubular member, the trocar coupling assembly including:
        a housing having opposed openings, and
        a passage defined between the opposed openings of the housing, the passage including internal threads; and
    a trocar assembly including:
        a sleeve having an outer surface, the outer surface including a slot extending therethrough and external threads, the external threads complimentary to the internal threads of the passage such that rotation of the sleeve relative to the housing translates the trocar assembly axially with respect to the housing, and
        a trocar disposed in a lumen of the sleeve.

15. A shaft for use with a surgical stapler, the shaft comprising:
    a tubular member, the tubular member including an opening extending through an outer wall thereof;
    a housing disposed in the tubular member, the housing having opposed openings along a longitudinal axis thereof;
    a passage defined between the opposed openings of the housing, the passage configured to slidably receive a trocar assembly therethrough;
    a bore extending through the housing in an orientation transverse to the passage, the bore in communication with the opening; and
    a fastener insertable through the opening and the bore, the fastener including a head and a shaft extending therefrom, the shaft including threads on a portion thereof, a distal portion of the shaft insertable into a retention slot of a sleeve of a trocar assembly to fix an axial position of a trocar assembly with respect to the housing.

\* \* \* \* \*